(12) United States Patent
Jackson et al.

(10) Patent No.: US 11,834,634 B2
(45) Date of Patent: *Dec. 5, 2023

(54) PHOSPHATE-FREE AUTOMATIC DISHWASHING DETERGENT COMPOSITIONS HAVING A PROTEASE AND A COMPLEXING AGENT

(71) Applicant: The Procter & Gamble Company, Cincinnati, OH (US)

(72) Inventors: Michelle Jackson, Newcastle upon Tyne (GB); Eva Maria Perez-Prat de Vinuesa, Newcastle upon Tyne (GB); David John Tarbit, Newcastle upon Tyne (GB); Philip Frank Souter, Northumberland (GB); Lilia Maria Babe, Emerald Hills, CA (US); David Aaron Estell, San Mateo, CA (US); Frits Goedegebuur, Vlaardingen (NL); Harm Jan Mulder, Voorhout (NL); Sina Pricelius, Leiden (NL); Lydia Dankmeyer, Rotterdam (NL); Thijs Kaper, Half Moon Bay, CA (US); Hatice Billur Engin, Mountain View, CA (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 16/217,069

(22) Filed: Dec. 12, 2018

(65) Prior Publication Data
US 2019/0185788 A1 Jun. 20, 2019

(30) Foreign Application Priority Data

Dec. 19, 2017 (EP) .................................... 17208450
Dec. 19, 2017 (EP) .................................... 17208474
Dec. 19, 2017 (EP) .................................... 17208519

(51) Int. Cl.
| | |
|---|---|
| *C11D 3/386* | (2006.01) |
| *C12N 9/64* | (2006.01) |
| *C12N 9/26* | (2006.01) |
| *C11D 3/20* | (2006.01) |
| *C11D 3/33* | (2006.01) |
| *C11D 3/39* | (2006.01) |
| *C11D 3/22* | (2006.01) |
| *C12N 9/28* | (2006.01) |

(52) U.S. Cl.
CPC ............ *C11D 3/386* (2013.01); *C11D 3/2086* (2013.01); *C11D 3/225* (2013.01); *C11D 3/33* (2013.01); *C11D 3/3905* (2013.01); *C12N 9/2414* (2013.01); *C12N 9/2417* (2013.01); *C12N 9/6424* (2013.01); *C12N 9/6489* (2013.01); *C12Y 304/21062* (2013.01); *C12Y 302/01001* (2013.01); *C12Y 304/16* (2013.01); *C12Y 304/17* (2013.01)

(58) Field of Classification Search
CPC .. C12N 9/6424; C12N 9/2414; C12N 9/2417; C12N 9/6489; C11D 3/386; C11D 3/2086; C11D 3/33; C11D 3/3905; C12Y 304/21062; C12Y 302/01001; C12Y 304/16; C12Y 304/17
USPC .......................................................... 435/222
See application file for complete search history.

(56) References Cited

U.S. PATENT DOCUMENTS

| | | |
|---|---|---|
| 2009/0233832 A1 | 9/2009 | Souter |
| 2016/0122691 A1 | 5/2016 | Meek |
| 2017/0321157 A1 | 11/2017 | Jackson et al. |
| 2018/0216090 A1 | 8/2018 | Mulder et al. |
| 2018/0237761 A1 | 8/2018 | Babe et al. |
| 2019/0330610 A1* | 10/2019 | Babe ........................ C12N 9/54 |

FOREIGN PATENT DOCUMENTS

| | | | |
|---|---|---|---|
| JP | 2005534280 A | 11/2005 | |
| JP | 2009543577 A | 12/2009 | |
| JP | 2011511879 A | 4/2011 | |
| JP | 2012517501 A | 8/2012 | |
| WO | 2017215925 A1 | 12/2017 | |
| WO | 2018118950 | * 6/2018 | ............... C12N 9/54 |

OTHER PUBLICATIONS

USPTO alignment SID1 vs SID102 of 62437509; priority doc of WO2018118950. Performed Apr. 1, 2021.*
International Search Report and Written Opinion; Application Ser. No. PCT/US2018/065917; dated May 13, 2019; 18 pages.
Extended European Search Report; Application No. 17208519.3-1105; dated Oct. 18, 2022; 11 pages.

* cited by examiner

*Primary Examiner* — Ganapathirama Raghu
(74) *Attorney, Agent, or Firm* — Carolyn S. Powell

(57) ABSTRACT

A phosphate-free automatic dishwashing cleaning composition comprising i) a protease wherein the protease is a variant having at least 60% identity with the amino acid sequence of SEQ ID NO:1 and comprising at least one amino acid substitution (using the SEQ ID NO: 1 numbering) selected from the group consisting of X54T; X126A, D, G, V, E, K, I; X127E, S, T, A, P, G, C; and X128E, C, T, D, P, G, L, Y, N; and ii) from 10 to 50% by weight of the composition of a complexing agent system comprising from 0 to less than 30% by weight of the composition of citric acid.

9 Claims, No Drawings
Specification includes a Sequence Listing.

```
                            SEQUENCE LISTING

<160> NUMBER OF SEQ ID NOS: 10

<210> SEQ ID NO 1
<211> LENGTH: 269
<212> TYPE: PRT
<213> ORGANISM: Bacillus gibsonii

<400> SEQUENCE: 1

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Ser Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Asn Ala Glu Leu Tyr Ala Val Lys Val Leu Gly Ala
                85                  90                  95

Asn Gly Ser Gly Ser Val Ser Gly Ile Ala Gln Gly Leu Glu Trp Ala
            100                 105                 110

Ala Thr Asn Asn Met His Ile Ala Asn Met Ser Leu Gly Ser Asp Phe
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255
```

Phe Gly Ser Gly Leu Val Asn Ala Glu Ala Ala Thr Arg
         260                 265

<210> SEQ ID NO 2
<211> LENGTH: 269
<212> TYPE: PRT
<213> ORGANISM: Bacillus lentus

<400> SEQUENCE: 2

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

<210> SEQ ID NO 3
<211> LENGTH: 269
<212> TYPE: PRT
<213> ORGANISM: Bacillus clausii

<400> SEQUENCE: 3

Ala Gln Ser Val Pro Trp Gly Ile Arg Arg Val Gln Ala Pro Thr Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

```
Phe Val Pro Gly Glu Pro Ser Thr Gln Asp Gly Asn Gly His Gly Thr
 50                  55                  60

His Ala Ala Gly Thr Ile Ala Ala Leu Asn Asn Ser Ile Gly Val Leu
 65                  70                  75                  80

Gly Val Ala Pro Ser Ala Glu Leu Tyr Ala Val Lys Val Leu Gly Ala
                 85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
        130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asp Gly Thr Ser Met Ala Thr Pro His Val Ala Gly Ala
        210                 215                 220

Ala Ala Leu Val Lys Gln Lys Asn Pro Ser Trp Ser Asn Val Arg Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

<210> SEQ ID NO 4
<211> LENGTH: 269
<212> TYPE: PRT
<213> ORGANISM: Bacillus lentus

<400> SEQUENCE: 4

Ala Gln Ser Val Pro Trp Gly Ile Ser Arg Val Gln Ala Pro Ala Ala
 1               5                  10                  15

His Asn Arg Gly Leu Thr Gly Ser Gly Val Lys Val Ala Val Leu Asp
                 20                  25                  30

Thr Gly Ile Ser Thr His Pro Asp Leu Asn Ile Arg Gly Gly Ala Ser
             35                  40                  45

Phe Val Pro Gly Glu Pro Ser Thr Gln Asp Gly Asn Gly His Gly Thr
 50                  55                  60

His Val Ala Gly Thr Ile Ala Ala Leu Asn Asn Ser Ile Gly Val Leu
 65                  70                  75                  80

Gly Val Ala Pro Ser Ala Glu Leu Tyr Ala Val Lys Val Leu Gly Ala
                 85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
        130                 135                 140

Val Leu Val Val Ala Ala Ser Gly Asn Ser Gly Ala Ser Ser Ile Ser
145                 150                 155                 160
```

Tyr Pro Ala Arg Tyr Ala Asn Ala Met Ala Val Gly Ala Thr Asp Gln
            165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
            195                 200                 205

Ala Ser Leu Asn Gly Thr Ser Met Ala Thr Pro His Val Ala Gly Ala
            210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
            245                 250                 255

Tyr Gly Ser Gly Leu Val Asn Ala Glu Ala Ala Thr Arg
            260                 265

<210> SEQ ID NO 5
<211> LENGTH: 269
<212> TYPE: PRT
<213> ORGANISM: Artificial
<220> FEATURE:
<223> OTHER INFORMATION: Variant of SEQ ID NO:2

<400> SEQUENCE: 5

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Asn Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Val Met His Val Ala Asn Leu Ser Leu Gly Leu Gln Ala
            115                 120                 125

Pro Ser Ala Thr Leu Glu Gln Ala Val Asn Ser Ala Thr Ser Arg Gly
        130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
            165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
            195                 200                 205

Ala Ser Leu Asn Gly Thr Ser Met Ala Thr Pro His Val Ala Gly Ala
            210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
            245                 250                 255

Tyr Gly Ser Gly Leu Val Asn Ala Glu Ala Ala Thr Arg
            260                 265

<210> SEQ ID NO 6
<211> LENGTH: 269
<212> TYPE: PRT
<213> ORGANISM: Artificial
<220> FEATURE:
<223> OTHER INFORMATION: Variant of SEQ ID NO:2

<400> SEQUENCE: 6

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asp Asn Ser Ile Gly Val Leu
65                  70                  75                  80

Gly Val Ala Pro Arg Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Arg Met His Val Ala Asn Leu Ser Leu Gly Leu Gln Ala
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

<210> SEQ ID NO 7
<211> LENGTH: 270
<212> TYPE: PRT
<213> ORGANISM: Artificial
<220> FEATURE:
<223> OTHER INFORMATION: Variant of SEQ ID NO:2

<400> SEQUENCE: 7

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp

```
            20                  25                  30
Thr Gly Ile Ser Thr His Pro Asp Leu Asn Ile Arg Gly Gly Ala Ser
         35                  40                  45
Phe Val Pro Gly Glu Pro Ser Thr Gln Asp Gly Asn Gly His Gly Thr
     50                  55                  60
His Val Ala Gly Thr Ile Ala Ala Leu Asn Asn Ser Ile Gly Val Leu
 65                  70                  75                  80
Gly Val Ala Pro Ser Ala Glu Leu Tyr Ala Val Lys Val Leu Gly Ala
                 85                  90                  95
Ser Glu Gly Ser Gly Ser Val Ser Ser Ile Ala Gln Gly Leu Glu Trp
            100                 105                 110
Ala Gly Asn Asn Gly Met His Val Ala Asn Leu Ser Leu Gly Ser Pro
        115                 120                 125
Ser Pro Ser Ala Thr Leu Glu Gln Ala Val Asn Ser Ala Thr Ser Arg
    130                 135                 140
Gly Val Leu Val Val Ala Ala Ser Gly Asn Ser Gly Ala Gly Ser Ile
145                 150                 155                 160
Ser Tyr Pro Ala Arg Tyr Ala Asn Ala Met Ala Val Gly Ala Thr Asp
                165                 170                 175
Gln Asn Asn Asn Arg Ala Ser Phe Ser Gln Tyr Gly Ala Gly Leu Asp
            180                 185                 190
Ile Val Ala Pro Gly Val Asn Val Gln Ser Thr Tyr Pro Gly Ser Thr
        195                 200                 205
Tyr Ala Ser Leu Asn Gly Thr Ser Met Ala Thr Pro His Val Ala Gly
    210                 215                 220
Ala Ala Ala Leu Val Lys Gln Lys Asn Pro Ser Trp Ser Asn Val Gln
225                 230                 235                 240
Ile Arg Asn His Leu Lys Asn Thr Ala Thr Ser Leu Gly Ser Thr Asn
                245                 250                 255
Leu Tyr Gly Ser Gly Leu Val Asn Ala Glu Ala Ala Thr Arg
            260                 265                 270

<210> SEQ ID NO 8
<211> LENGTH: 270
<212> TYPE: PRT
<213> ORGANISM: Artificial
<220> FEATURE:
<223> OTHER INFORMATION: Variant of SEQ ID NO:2

<400> SEQUENCE: 8

Ala Gln Ser Val Pro Trp Gly Ile Ser Arg Val Gln Ala Pro Ala Ala
  1               5                  10                  15
His Asn Arg Gly Leu Thr Gly Ser Gly Val Lys Val Ala Val Leu Asp
             20                  25                  30
Thr Gly Ile Ser Thr His Pro Asp Leu Asn Ile Arg Gly Gly Ala Ser
         35                  40                  45
Phe Val Pro Gly Glu Pro Ser Thr Gln Asp Gly Asn Gly His Gly Thr
     50                  55                  60
His Val Ala Gly Thr Ile Ala Ala Leu Asn Asn Ser Ile Gly Val Leu
 65                  70                  75                  80
Gly Val Ala Pro Ser Ala Glu Leu Tyr Ala Val Lys Val Leu Gly Ala
                 85                  90                  95
Ala Asp Gly Ser Gly Ser Val Ser Ser Ile Ala Gln Gly Leu Glu Trp
            100                 105                 110
Ala Gly Asn Asn Gly Met His Val Ala Asn Leu Ser Leu Gly Ser Pro
```

```
             115                 120                 125
Ser Pro Ser Ala Thr Leu Glu Gln Ala Val Asn Ser Ala Thr Ser Arg
130                 135                 140

Gly Val Leu Val Val Ala Ala Ser Gly Asn Ser Gly Ala Gly Ser Ile
145                 150                 155                 160

Ser Tyr Pro Ala Arg Tyr Ala Asn Ala Met Ala Val Gly Ala Thr Asp
                165                 170                 175

Gln Asn Asn Asn Arg Ala Ser Phe Ser Gln Tyr Gly Ala Gly Leu Asp
                180                 185                 190

Ile Val Ala Pro Gly Val Asn Val Gln Ser Thr Tyr Pro Gly Ser Thr
                195                 200                 205

Tyr Ala Ser Leu Asn Gly Thr Ser Met Ala Thr Pro His Val Ala Gly
210                 215                 220

Ala Ala Ala Leu Val Lys Gln Lys Asn Pro Ser Trp Ser Asn Val Gln
225                 230                 235                 240

Ile Arg Asn His Leu Lys Asn Thr Ala Thr Ser Leu Gly Ser Thr Asn
                245                 250                 255

Leu Tyr Gly Ser Gly Leu Val Asn Ala Glu Ala Ala Thr Arg
                260                 265                 270

<210> SEQ ID NO 9
<211> LENGTH: 269
<212> TYPE: PRT
<213> ORGANISM: Artificial
<220> FEATURE:
<223> OTHER INFORMATION: Variant of SEQ ID NO:2

<400> SEQUENCE: 9

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
                35                  40                  45

Phe Val Pro Gly Glu Pro Ser Thr Gln Asp Gly Asn Gly His Gly Thr
50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
                100                 105                 110

Gly Asn Asn Gly Met His Val Ala Asn Leu Ser Leu Gly Ser Pro Ser
                115                 120                 125

Pro Ser Ala Thr Leu Glu Gln Ala Val Asn Ser Ala Thr Ser Arg Gly
130                 135                 140

Val Leu Val Val Ala Ala Ser Gly Asn Ser Gly Ala Gly Ser Ile Ser
145                 150                 155                 160

Ala Pro Ala Ser Tyr Ala Asn Ala Met Ala Val Gly Ala Thr Asp Gln
                165                 170                 175

Asn Asn Asn Arg Ala Ser Phe Ser Gln Tyr Gly Pro Gly Leu Asp Ile
                180                 185                 190

Val Ala Pro Gly Val Asn Val Gln Ser Thr Tyr Pro Gly Ser Thr Tyr
                195                 200                 205

Ala Ser Leu Asn Gly Thr Ser Met Ala Thr Pro His Val Ala Gly Ala
```

```
                    210                 215                 220
Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                    245                 250                 255

Tyr Gly Ser Gly Leu Val Asn Ala Glu Ala Ala Thr Arg
                260                 265

<210> SEQ ID NO 10
<211> LENGTH: 269
<212> TYPE: PRT
<213> ORGANISM: Artificial
<220> FEATURE:
<223> OTHER INFORMATION: Variant of SEQ ID NO:2

<400> SEQUENCE: 10

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Asn Ala Glu Leu Tyr Ala Val Lys Val Leu Gly Ala
                85                  90                  95

Ser Gly Met Gly Ser Val Ser Ser Ile Ala Gln Gly Leu Glu Trp Ala
                100                 105                 110

Gly Asn Asn Val Met His Val Ala Asn Leu Ser Leu Gly Leu Gln Ala
            115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
                180                 185                 190

Val Ala Pro Gly Val Asn Val Gln Ser Thr Tyr Pro Gly Ser Thr Tyr
            195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
                260                 265
```

PHOSPHATE-FREE AUTOMATIC DISHWASHING DETERGENT COMPOSITIONS HAVING A PROTEASE AND A COMPLEXING AGENT

PARTIES OF JOINT RESEARCH AGREEMENT

The claimed subject matter of the present application was made by or on behalf of the below parties to a joint research agreement. The joint research agreement was in effect on or before the date the claimed invention was made and the claimed invention was made as a result of activities undertaken with the scope of the joint research agreement. The parties to the joint research agreement are The Procter & Gamble Company and Danisco US Inc.

FIELD OF THE INVENTION

The present invention is in the field of detergents. In particular, it relates to phosphate-free automatic dishwashing detergent compositions comprising new proteases. The compositions provide improved cleaning under a plurality of conditions versus compositions comprising conventional proteases.

BACKGROUND OF INVENTION

There is a permanent desire to improve the performance of automatic dishwashing compositions and their environmental profile.

Due to environmental concerns phosphate is increasingly being replaced by biodegradable complexing agents. These complexing agents can have a strong binding capacity for metals and/or are used in high levels and can negatively affect the performance of enzymes, in particular complexing agents can negatively affect proteases by extracting the structural calcium metal ions of the protease. The proteases can be affected in product and/or in-use. They can be more affected under fully built or overbuilt conditions, i.e., when a composition comprises high level of complexing agent and the composition is used in soft water because there will be more free builder to complex with the structural calcium metal ions of the protease. For the toughest items, consumers would usually select hot, long automatic dishwashing cycles. These cycles create a lot of stress on enzymes.

Automatic dishwashing compositions can be designed to have optimum performance under certain in-use conditions, for example a composition can be designed to have optimum performance in a soft water cycle, however a composition that has optimum performance in soft water might not have optimum performance in a hard water cycle and vice versa.

The object of the present invention is to provide a phosphate-free automatic dishwashing composition that provides better cleaning when used in soft or hard water and preferably under different water hardness's. It is also desirable that the composition provides improved performance even under stressed conditions such as heavily soiled load washed in hot, long cycles.

SUMMARY OF THE INVENTION

According to the first aspect of the present invention, there is provided a phosphate-free automatic dishwashing cleaning composition. The composition comprises a complexing agent system and a novel protease. The composition presents improved cleaning performance on egg and sugary stains such as crème brulee. The composition performs really well even when soft water is used in the automatic dishwashing process and even when a hot long cycle is used.

According to the second aspect of the present invention, there is provided a phosphate-free automatic dishwashing cleaning composition. The composition comprises a complexing agent system, a high level of a bleaching system and a specific protease. The composition presents improved performance even when soft water and/or high temperatures and/or long cycles are used in automatic dishwashing.

According to the third aspect of the present invention, there is provided a phosphate-free automatic dishwashing cleaning composition. The composition comprises a complexing agent system and a specific protease. The composition presents improved performance even when hard water is used in the automatic dishwashing process and the dishwashing program used is hot (the was temperature is above 50° C.) and long (the main wash is longer than 25 mins) and the dishware is heavily soiled. Even under these very stressed conditions the composition of the invention provides very good shine and cleaning, including very good removal of protein and starch based soils.

DETAILED DESCRIPTION OF THE INVENTION

The present invention encompasses automatic dishwashing cleaning compositions. Two of the compositions of the invention are phosphate-free and comprises a complexing agent system and a protease. The compositions deliver improved cleaning versus cleaning compositions comprising conventional proteases under a plurality of conditions. The compositions provide good proteinaceous cleaning, in particular on egg and crème brulee soils. The invention also encompasses methods of automatic dishwashing with soft water and also methods of automatic dishwashing with soft water using hot, long cycles.

The present invention also encompasses a composition that is phosphate-free and comprises a complexing agent system comprising a strong complexing agent, a protease and an amylase. The composition successfully provides excellent shine along with good protein and starch soil removal, including good removal of mixed protein/starch soils. The composition provides good cleaning, in particular on egg, baked cheese and starch. The invention also encompasses methods of automatic dishwashing with hard water.

By "soft" water is herein meant water having a hardness of less than about 2 gpg (34.3 ppm). Grain per gallon (gpg) is a unit of water hardness defined as 1 grain (64.8 milligrams) of calcium carbonate dissolved in 1 US gallon of water (3.785412 L). It translates into 17.1 parts per million (ppm).

By "hard" water is herein meant water having a hardness of more than 12 (205.7 ppm), preferably more than 15 (257.1 ppm) and more preferably more than 19 gpg (325.6 ppm). Grain per gallon (gpg) is a unit of water hardness defined as 1 grain (64.8 milligrams) of calcium carbonate dissolved in 1 US gallon of water (3.785412 L). It translates into 17.1 parts per million (ppm).

By "hot" cycle is herein understood a dishwashing program in which the main cycle is performed at a temperature above 50° C., preferably above 55° C.

By "long" cycle is herein understood a dishwashing program in which the main cycle has a duration of at least 25, preferably at least 30 and more preferably at least 35 minutes and especially at least 45 minutes.

The compositions of the invention comprise a variant protease, the variant proteases have a defined percentage of identity with respect to a reference protease (proteases of SEQ ID NO: 1 to 10).

The proteases of the composition of the invention are herein sometimes referred to as "the protease of the invention". The proteases having any of sequences ID NO:1 to 10 are herein sometimes referred to as "the reference protease".

The relatedness between two amino acid sequences or between two nucleotide sequences is described by the parameter "sequence identity".

The term "variant" means a protease comprising a mutation, i.e., a substitution, insertion, and/or deletion, at one or more (e.g., several) positions relative to the reference protease. A substitution means replacement of the amino acid occupying a position with a different amino acid; a deletion means removal of the amino acid occupying a position; and an insertion means adding an amino acid adjacent to and immediately following the amino acid occupying a position. The variants of the present invention have at least 60%, preferably at least 70%, more preferably a least 75% and especially 90% identity with the reference protease.

In preferred embodiments, the variant presents at least 90%, more preferably at least 92% identity with the protease of SEQ ID NO: 1. SEQ ID NO: 1 corresponds to $B.$ $gibsonii$-clade subtilisin Bgi02446. In other embodiments, the variant presents at least 90%, more preferably at least 92% identity with the protease of SEQ ID NO: 2. SEQ ID NO: 2 corresponds to $B.$ $lentus$ subtilisin. In other embodiments, the variant presents at least 90%, more preferably at least 92% identity with one of the proteases of sequences SEQ ID NO: 3-10.

The term "wild-type" protease means a protease expressed by a naturally occurring microorganism, such as a bacterium, yeast, or filamentous fungus found in nature.

Enzyme Related Terminology
Nomenclature for Amino Acid Modifications

In describing enzyme variants herein, the following nomenclature is used for ease of reference: Original amino acid(s): position(s): substituted amino acid(s).

According to this nomenclature, for instance the substitution of glutamic acid for glycine in position 195 is shown as G195E. A deletion of glycine in the same position is shown as G195*, and insertion of an additional amino acid residue such as lysine is shown as G195GK. Where a specific enzyme contains a "deletion" in comparison with other enzyme and an insertion is made in such a position this is indicated as *36D for insertion of an aspartic acid in position 36. Multiple mutations are separated by pluses, i.e.: S99G+V102N, representing mutations in positions 99 and 102 substituting serine and valine for glycine and asparagine, respectively. Where the amino acid in a position (e.g. 102) may be substituted by another amino acid selected from a group of amino acids, e.g. the group consisting of N and I, this will be indicated by V102N, I.

In all cases, the accepted IUPAC single letter or triple letter amino acid abbreviation is employed.

Protease Amino Acid Numbering

The numbering used in this patent is versus the sequences shown and not the BPN' numbering.

Amino Acid Identity

The relatedness between two amino acid sequences is described by the parameter "identity". For purposes of the present invention, the alignment of two amino acid sequences is determined by using the Needle program from the EMBOSS package (http://emboss.org) version 2.8.0. The Needle program implements the global alignment algorithm described in Needleman, S. B. and Wunsch, C. D. (1970) J. Mol. Biol. 48, 443-453. The substitution matrix used is BLOSUM62, gap opening penalty is 10, and gap extension penalty is 0.5.

The degree of identity between an amino acid sequence of an enzyme used herein ("invention sequence") and a different amino acid sequence ("foreign sequence") is calculated as the number of exact matches in an alignment of the two sequences, divided by the length of the "invention sequence" or the length of the "foreign sequence", whichever is the shortest. The result is expressed in percent identity. An exact match occurs when the "invention sequence" and the "foreign sequence" have identical amino acid residues in the same positions of the overlap. The length of a sequence is the number of amino acid residues in the sequence.

The term "succinate based compound" and "succinic acid based compound" are used interchangeably herein.

As used herein, articles such as "a" and "an" when used in a claim, are understood to mean one or more of what is claimed or described.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

The Proteases of the Invention
Protease of the First Aspect of the Invention

The protease of the first aspect of the present invention has at least 60%, preferably at least 70%, more preferably at least 75% identity with the protease of SEQ ID NO: 1.

The protease of the first aspect of the present invention comprises at least one amino acid substitution, preferably at least two, more preferably at least three amino acid substitution(s) (using the SEQ ID NO 1 numbering) selected from the group consisting of:
X54T;
X126A, D, G, V, E, K, I;
X127E, S, T, A, P, G, C; and
X128E, C, T, D, P, G, L, Y, N.

Preferably the variant has at least 90%, preferably at least 92% identity with the amino acid sequence of SEQ ID NO:1 and comprises at least one, preferably at least two, more preferably at least three amino acid substitution(s) (using the SEQ ID NO:1 numbering) selected from the group consisting of:
P54T;
S126A, D, G, V, E, K, I;
D127E, S, T, A, P, G, C; and
F128E, C, T, D, P, G, L, Y, N.

Preferably, the variant comprises at least one amino acid substitution (using the SEQ ID NO:1 numbering) selected from the group consisting of: S126A, D127E and F128G, more preferably at least two and preferably three amino acid substitutions, i.e. S126A, D127E and F128G. The variant can also comprise the P54T substitution. Also preferred are variants comprising the following substitutions: P54T, S126A, D127E and F128G. Also preferred are variants comprising the following substitutions: I80V, S126A, D127E and F128G. Also preferred are variants comprising the following substitutions: I80V, S126A, D127E, F128G and M211L. A preferred variant comprises the following substitutions P54T, I80V, S126A, D127E, F128G and M211L.

Preferably, the variant further comprises at least one amino acid substitution (using the SEQ ID NO:1 numbering) selected from X114Q and X114C, preferably T114Q.

Preferably, the variant further comprises at least one and more preferably at least two and more preferably three amino acid substitution(s) (using the SEQ ID NO:1 numbering) selected from the group consisting of I80V, R, Y; S99 R, D, E, I, K, L; N85S, C, D, I, K; E87D, C.

A specially preferred variant comprises at least one amino acid substitution (using the SEQ ID NO:1 numbering) selected from the group consisting of S39E, S99R, S126A+D127E+F128G and N242D, more preferably at least two, more preferably at least three and specially all the substitutions in the group, i.e., S39E-S99R-S126A-D127E-F128G and N242D. Specially preferred variants comprise the following substitutions S39E-I80V-S99R-S126A-D127E-F128G, M211L and N242D.

Preferably, the variant has at least 90% identity with the amino acid sequence of SEQ ID NO:1 and said variant further comprises at least one substitution (using the SEQ ID NO:1 numbering), more preferably at least two and especially at least three or more than three substitutions selected from the group consisting of T3V, T9R, A15T, V66A, N74D, N85R, N97NE, N97AD, N97D/G, S99G/M, S101A, V102E/I, N116V/R, S126L, D127Q, F128A, G157S, Y161A, R164S, T188P, V199I, Q200C/E/I/K/T/V/W/L, Y203W, N212D, M216S/F, Q239R and T249R.

Especially preferred variants for use in the composition of the invention are selected from the group consisting of variants having at least 90%, more preferably at least 92% identity with the amino acid sequence SEQ ID:1 and comprising substitutions (using the SEQ ID NO:1 numbering) selected from the group consisting of:

1) T056Y-S099R-S126A-D127E-F128G
2) S039E-I080V-S099R-S126A-D127E-F128G-M211L
3) S039E-P054T-S099R-S126A-D127E-F128G-M211L
4) S039E-I043V-S099R-S126A-D127E-F128G-M211L
5) S039E-N042R-S099R-S126A-D127E-F128G
6) S039E-I080V-S099R-S126A-D127E-F128G
7) S039E-S099R-S126A-D127E-F128G-M211L
8) S039E-N085S-S099R-S126A-D127E-F128G-M211L
9) S039E-T056Y-S099R-S126A-D127E-F128G-M211L
10) S039E-A047V-S099R-S126A-D127E-F128G-M211L
11) S039E-S099R-S126A-D127E-F128G-Y203W
12) A037T-S039E-S099R-S126A-D127E-F128G-M211L
13) S039E-S099R-S126A-D127E-F128G-V199I
14) A037T-S039E-I043V-A047V-P054T-T056Y-I080V-N085S-E087D-S099R-T114Q-S126A-D127E-F128G
15) S039E-I043V-A047V-P054T-T056Y-I080V-N085S-E087D-S099R-S126A-D127E-F128G-N242D
16) A037T-S039E-I043V-A047V-T056Y-I080V-N085S-E087D-S099R-T114Q-S126A-D127E-F128G
17) A037T-S039E-I043V-A047V-P054T-T056Y-I080V-N085S-E087D-S099R-S126A-D127E-F128G
18) S039E-I043V-S099R-S126A-D127E-F128G
19) S039E-S099R-S126A-D127E-F128G-N253D
20) T009E-S039E-S099R-S126A-D127E-F128G
21) S039E-S099R-S126A-D127E-F128G-S255W
22) A037T-S039E-I043V-A047V-P054T-T056Y-I080V-N085S-S099R-S126A-D127E-F128G-N242D
23) A037T-S039E-I043V-P054T-T056Y-I080V-N085S-E087D-S099R-S126A-D127E-F128G-N242D
24) S039E-I043V-A047V-T056Y-I080V-N085S-E087D-S099R-S126A-D127E-F128G-N242D
25) S039E-I043V-A047V-T056Y-I080V-N085S-E087D-S099R-T114Q-S126A-D127E-F128G-N242D
26) S039E-T056Y-S099R-S126A-D127E-F128G
27) A037T-S039E-I043V-A047V-T056Y-I080V-N085S-E087D-S099R-S126A-D127E-F128G
28) A037T-S039E-I043V-P054T-T056Y-I080V-N085S-E087D-S099R-T114Q-S126A-D127E-F128G-N242D
29) A037T-S039E-I043V-T056Y-I080V-N085S-E087D-S099R-T114Q-S126A-D127E-F128G-N242D
30) A037T-S039E-I043V-A047V-I080V-N085S-E087D-S099R-T114Q-S126A-D127E-F128G-N242D
31) A037T-S039E-I043V-A047V-P054T-I080V-N085S-E087D-S099R-S126A-D127E-F128G-N242D
32) A037T-S039E-I043V-A047V-T056Y-I080V-N085S-E087D-S099R-S126A-D127E-N242D
33) A037T-S039E-I043V-T056Y-I080V-N085S-E087D-S099R-S126A-D127E-F128G-N242D
34) A037T-S039E-I043V-A047V-T056Y-I080V-N085S-E087D-S099R-T114Q-S126A-D127E-N242D
35) S039E-N085S-S099R-S126A-D127E-F128G
36) A037T-S039E-I043V-A047V-P054T-I080V-N085S-E087D-S099R-T114Q-S126A-D127E-F128G-N242D
37) A037T-S039E-I043V-A047V-P054T-T056Y-I080V-N085S-S099R-T114Q-S126A-D127E-F128G-N242D
38) A037T-S039E-I043V-A047V-P054T-T056Y-I080V-N085S-E087D-S099R-T114Q-S126A-D127E-N242D
39) A037T-S039E-I043V-A047V-P054T-T056Y-I080V-N085S-E087D-S126A-D127E-F128G-N242D
40) A037T-S039E-I043V-A047V-T056Y-I080V-N085S-E087D-S099R-S126A-F128G-N242D
41) A037T-S039E-I043V-A047V-T056Y-I080V-E087D-S099R-T114Q-S126A-D127E-F128G-N242D
42) S039E-S099R-T114Q-S126A-D127E-F128G
43) A037T-S039E-I043V-A047V-P054T-T056Y-I080V-N085S-E087D-S099R-S126A-D127E-N242D
44) A037T-S039E-I043V-A047V-T056Y-I080V-N085S-E087D-S099R-S126A-D127E-F128G-N242D
45) A037T-S039E-I043V-A047V-P054T-T056Y-I080V-N085S-E087D-S099R-T114Q-D127E-F128G-N242D
46) A037T-S039E-I043V-A047V-T056Y-I080V-N085S-S099R-T114Q-S126A-D127E-F128G-N242D
47) S039E-A047V-S099R-S126A-D127E-F128G
48) A037T-S039E-I043V-A047V-T056Y-I080V-N085S-S099R-S126A-D127E-F128G-N242D
49) A037T-S039E-I043V-A047V-T056Y-S099R-T114Q-S126A-D127E-F128G
50) A037T-S039E-I043V-A047V-P054T-T056Y-I080V-E087D-S099R-S126A-D127E-F128G-N242D
51) S039E-P054T-S099R-S126A-D127E-F128G
52) A037T-S039E-I043V-A047V-P054T-T056Y-I080V-N085S-E087D-S099R-T114Q-S126A-D127E-F128G-N242D
53) A037T-S039E-I043V-A047V-I080V-N085S-E087D-S099R-S126A-D127E-F128G-N242D
54) A037T-S039E-I043V-A047V-T056Y-I080V-E087D-S099R-S126A-D127E-F128G-N242D
55) A037T-S039E-I043V-A047V-T056Y-I080V-N085S-E087D-S099R-T114Q-D127E-F128G-N242D
56) A037T-S039E-I043V-A047V-P054T-T056Y-I080V-N085S-E087D-S099R-D127E-F128G-N242D
57) S039E-E087D-S099R-S126A-D127E-F128G
58) A037T-S039E-I043V-A047V-T056Y-I080V-N085S-E087D-S099R-D127E-F128G-N242D
59) A037T-S039E-I043V-A047V-P054T-T056Y-I080V-N085S-E087D-S099R-T114Q-S126A-F128G-N242D

60) A037T-S039E-S099R-S126A-D127E-F128G
61) A037T-S039E-I043V-A047V-P054T-T056Y-I080V-E087D-S099R-T114Q-S126A-D127E-F128G-N242D
62) A037T-S039E-I043V-A047V-P054T-T056Y-I080V-N085S-E087D-S099R-S126A-D127E-F128G-N242D
63) A037T-S039E-I043V-A047V-T056Y-I080V-N085S-E087D-S099R-T114Q-S126A-F128G-N242D
64) A037T-S039E-I043V-A047V-T056Y-S099R-S126A-D127E-F128G
65) A037T-S039E-I043V-A047V-P054T-T056Y-S099R-T114Q-S126A-D127E-F128G
66) A037T-S039E-A047V-P054T-T056Y-I080V-N085S-E087D-S099R-S126A-D127E-F128G-N242D
67) A037T-S039E-I043V-A047V-P054T-T056Y-I080V-N085S-E087D-S099R-S126A-F128G-N242D
68) A037T-S039E-I043V-A047V-P054T-T056Y-I080V-N085S-E087D-T114Q-S126A-D127E-F128G-N242D
69) A037T-S039E-I043V-A047V-T056Y-I080V-N085S-E087D-S126A-D127E-F128G-N242D
70) A037T-S039E-A047V-T056Y-I080V-N085S-E087D-S099R-T114Q-S126A-D127E-F128G-N242D
71) S039E-S099R-S126A-D127E-F128G
72) A037T-S039E-A047V-P054T-T056Y-I080V-N085S-E087D-S099R-T114Q-S126A-D127E-F128G-N242D
73) A037T-S039E-I043V-A047V-T056Y-I080V-N085S-E087D-T114Q-S126A-D127E-F128G-N242D
74) A037T-S039E-A047V-T056Y-I080V-N085S-E087D-S099R-S126A-D127E-F128G-N242D
75) S039E-S099R-S126A-D127E-F128G-Q256E
76) S039E-S099R-S126A-D127E-F128G-N242D
77) S039E-S099R-S126A-D127E-F128G-Q200L
78) A037T-S039E-I043V-A047V-P054T-T056Y-S099R-T114Q-S126A-D127E-F128G-N242D
79) A037T-S039E-I043V-A047V-P054T-T056Y-S099R-S126A-D127E-F128G-N242D
80) S039E-N074D-I080V-S099R-S126A-D127E-F128G
81) A037T-S039E-I043V-A047V-P054T-T056Y-N085S-E087D-S099R-S126A-D127E-F128G-N242D
82) A037T-S039E-I043V-A047V-T056Y-N085S-E087D-S099R-T114Q-S126A-D127E-F128G-N242D
83) A037T-S039E-I043V-A047V
84) A037T-S039E-I043V-A047V-N242D
85) S039E-P054T-N074D-S099R-S126A-D127E-F128G
86) S039E-A047V-N074D-S099R-S126A-D127E-F128G
87) A037T-S039E-I043V-A047V-P054T-T056Y-N085S-E087D-S099R-T114Q-S126A-D127E-F128G-N242D
88) S039E-N074D-S099R-T114Q-S126A-D127E-F128G
89) S039E-N074D-N085S-S099R-S126A-D127E-F128G
90) A037T-S039E-I043V-A047V-T056Y-N085S-E087D-S099R-S126A-D127E-F128G-N242D
91) S039E-N074D-E087D-S099R-S126A-D127E-F128G
92) S039E-I043V-N074D-S099R-S126A-D127E-F128G
93) S039E-T056Y-N074D-S099R-S126A-D127E-F128G
94) S039E-N074D-S099R-S126A-D127E-F128G-N242D

Other preferred variants for use in the composition of the invention are selected from the group consisting of variants having at least 90%, more preferably at least 92% identity with the amino acid sequence SEQ ID:1 and comprising substitutions (using the SEQ ID NO:1 numbering) selected from the group consisting of:
(a) A37T-S39E-I43V-A47V-T56Y-I80V-N85S-E87D-S99R-T114Q-S126D-D127S-F128A-N242D;
(b) A37T-S39E-I43V-A47V-T56Y-I80V-N85S-E87D-T114Q-S126G-D127T-F128E-N242D;
(c) A37T-S39E-I43V-A47V-T56Y-I80V-N85S-E87D-S99R-T114Q-D127A-F128C-N242D;
(d) A37T-S39E-I43V-A47V-P54T-T56Y-I80V-N85S-E87D-S99E-T114Q-S126T-F128A-N242D;
(e) A37T-S39E-I43V-A47V-P54T-T56Y-I80V-N85S-E87D-S99R-T114Q-S126V-D127A-F128T-N242D;
(f) A37T-S39E-I43V-A47V-P54T-T56Y-I80V-N85S-E87D-S99R-T114Q-F128E-N242D;
(g) A37T-S39E-I43V-A47V-T56Y-I80V-N85S-E87D-S99E-T114Q-D127E-F128G-N242D;
(h) A37T-S39E-I43V-A47V-P54T-T56Y-I80V-N85S-E87D-S99R-T114Q-S126T-D127E-F128A-N242D;
(i) A37T-S39E-I43V-A47V-T56Y-I80V-N85S-E87D-T114Q-D127P-F128E-N242D;
(j) A37T-S39E-I43V-A47V-P54T-T56Y-I80V-N85S-E87D-S99R-T114Q-S126G-D127E-F128D-N242D;
(k) A37T-S39E-I43V-A47V-T56Y-I80V-N85S-E87D-S99R-T114Q-F128E-N242D;
(l) A37T-S39E-I43V-A47V-T56Y-I80V-N85S-E87D-S99R-T114Q-S126T-D127E-F128E-N242D;
(m) A37T-S39E-I43V-A47V-P54T-T56Y-I80V-N85S-E87D-S99R-T114Q-D127G-F128P-N242D; and
(n) A37T-S39E-I43V-A47V-P54T-T56Y-I80V-N85S-E87D-S99R-T114Q-D127G-F128E-N242D.

In one embodiment, the variant has at least 90%, preferably at least 95% identity with the amino acid sequence of SEQ ID NO:2 and comprises at least one, preferably at least two, more preferably at least three amino acid substitution(s) (using the SEQ ID NO:2 numbering) selected from the group consisting of:
X54T;
X126A, D, G, V, E, K, I;
X127E, S, T, A, G, C; and
X128E, C, T, D, P, G, L, Y, N.
Preferably, from the group consisting of:
P54T;
S126A, D, G, V, E, K, I;
P127E, S, T, A, G, C; and
S128E, C, T, D, P, G, L, Y, N.

Preferably, the variant comprises at least one amino acid substitution (using the SEQ ID NO:2 numbering) selected from the group consisting of: S126A, P127E and S128G, more preferably at least two and preferably three amino acid substitutions, i.e. S126A, P127E and S128G. The variant can also comprise the P54T substitution. Other preferred variants comprise S126A, P127E, S128G and P54T mutations. Especially preferred variants comprise P54T, L80V, S126A, P127E and S128G.

Preferably, the variant further comprises at least one amino acid substitution (using the SEQ ID NO:2 numbering) selected from N114Q and N114C.

Preferably, the variant further comprises at least one and more preferably at least two and more preferably three amino acid substitution (using the SEQ ID NO:2 numbering) selected from the group consisting of S99 R, D, E, I, K, L; S85C, D, I, K and E87D, C.

An especially preferred variant comprises at least one amino acid substitution (using the SEQ ID NO:2 numbering) selected from the group consisting of S39E, L80V, S99R, S126A+P127E+S128G and N242D, more preferably at least two, more preferably at least three and specially all the substitutions, i.e., S39E-L80V-S99R-S126A-P127E-S128G and N242D.

Preferably, the variant has at least 90% identity with the amino acid sequence of SEQ ID NO:2 and said variant comprising at least one substitution (using the SEQ ID NO:2 numbering), more preferably at least two, more preferably at least three and especially at least more than three substitutions selected from the group consisting of S3V, S9R, A15T, V66A, N74D, S85N/R, S97SE, S97AD, S97D/G, S99G/M, S101A, V102E/I, G116V/R, S126L, P127Q, S128A, G157S, Y161A, R164S, A188P, V199I, Q200C/E/I/K/T/V/W/L, Y203W, L211D/C/M, N212D, M216S/F, Q239R and T249R.

Especially preferred variants for use in the composition of the invention are selected from the group consisting of variants having at least 90%, more preferably at least 92% identity with the amino acid sequence SEQ ID NO:2 and comprising substitutions (using the SEQ ID NO:2 numbering) selected from the group consisting of:

1) T056Y-S099R-S126A-P127E-S128G
2) P039E-L080V-S099R-S126A-P127E-S128G-M211L
3) P039E-P054T-S099R-S126A-P127E-S128G-M211L
4) P039E-I043V-S099R-S126A-P127E-S128G-M211L
5) P039E-N042R-S099R-S126A-P127E-S128G
6) P039E-L080V-S099R-S126A-P127E-S128G
7) P039E-S099R-S126A-P127E-S128G-M211L
8) P039E-S099R-S126A-P127E-S128G-M211L
9) P039E-T056Y-S099R-S126A-P127E-S128G-M211L
10) P039E-A047V-S099R-S126A-P127E-S128G-M211L
11) P039E-S099R-S126A-P127E-S128G-Y203W
12) P039E-S099R-S126A-P127E-S128G-M211L
13) P039E-S099R-S126A-P127E-S128G-V199I
14) P039E-I043V-A047V-P054T-T056Y-L080V-E087D-S099R-N114Q-S126A-P127E-S128G
15) P039E-I043V-A047V-P054T-T056Y-L080V-E087D-S099R-S126A-P127E-S128G-N242D
16) P039E-I043V-A047V-T056Y-L080V-E087D-S099R-N114Q-S126A-P127E-S128G
17) P039E-I043V-A047V-P054T-T056Y-L080V-E087D-S099R-S126A-P127E-S128G
18) P039E-I043V-S099R-S126A-P127E-S128G
19) P039E-S099R-S126A-P127E-S128G-N253D
20) T009E-P039E-S099R-S126A-P127E-S128G
21) P039E-S099R-S126A-P127E-S128G-S255W
22) P039E-I043V-A047V-P054T-T056Y-L080V-S099R-S126A-P127E-S128G-N242D
23) P039E-I043V-P054T-T056Y-L080V-E087D-S099R-S126A-P127E-S128G-N242D
24) P039E-I043V-A047V-T056Y-L080V-E087D-S099R-S126A-P127E-S128G-N242D
25) P039E-I043V-A047V-T056Y-L080V-E087D-S099R-N114Q-S126A-P127E-S128G-N242D
26) P039E-T056Y-S099R-S126A-P127E-S128G
27) P039E-I043V-A047V-T056Y-L080V-E087D-S099R-S126A-P127E-S128G
28) P039E-I043V-P054T-T056Y-L080V-E087D-S099R-N114Q-S126A-P127E-S128G-N242D
29) P039E-I043V-T056Y-L080V-E087D-S099R-N114Q-S126A-P127E-S128G-N242D
30) P039E-I043V-A047V-L080V-E087D-S099R-N114Q-S126A-P127E-S128G-N242D
31) P039E-I043V-A047V-P054T-L080V-E087D-S099R-S126A-P127E-S128G-N242D
32) P039E-I043V-A047V-T056Y-L080V-E087D-S099R-S126A-P127E-N242D
33) P039E-I043V-T056Y-L080V-E087D-S099R-S126A-P127E-S128G-N242D
34) P039E-I043V-A047V-T056Y-L080V-E087D-S099R-N114Q-S126A-P127E-N242D
35) P039E-S099R-S126A-P127E-S128G
36) P039E-I043V-A047V-P054T-L080V-E087D-S099R-N114Q-S126A-P127E-S128G-N242D
37) P039E-I043V-A047V-P054T-T056Y-L080V-S099R-N114Q-S126A-P127E-S128G-N242D
38) P039E-I043V-A047V-P054T-T056Y-L080V-E087D-S099R-N114Q-S126A-P127E-N242D
39) P039E-I043V-A047V-P054T-T056Y-L080V-E087D-S126A-P127E-S128G-N242D
40) P039E-I043V-A047V-T056Y-L080V-E087D-S099R-S126A-S128G-N242D
41) P039E-I043V-A047V-T056Y-L080V-E087D-S099R-N114Q-S126A-P127E-S128G-N242D
42) P039E-S099R-N114Q-S126A-P127E-S128G
43) P039E-I043V-A047V-P054T-T056Y-L080V-E087D-S099R-S126A-P127E-N242D
44) P039E-I043V-A047V-T056Y-L080V-E087D-S099R-S126A-P127E-S128G-N242D
45) P039E-I043V-A047V-P054T-T056Y-L080V-E087D-S099R-N114Q-P127E-S128G-N242D
46) P039E-I043V-A047V-T056Y-L080V-S099R-N114Q-S126A-P127E-S128G-N242D
47) P039E-A047V-S099R-S126A-P127E-S128G
48) P039E-I043V-A047V-T056Y-L080V-S099R-S126A-P127E-S128G-N242D
49) P039E-I043V-A047V-T056Y-S099R-N114Q-S126A-P127E-S128G
50) P039E-I043V-A047V-P054T-T056Y-L080V-E087D-S099R-S126A-P127E-S128G-N242D
51) P039E-P054T-S099R-S126A-P127E-S128G
52) P039E-I043V-A047V-P054T-T056Y-L080V-E087D-S099R-N114Q-P127E-S128G-N242D
53) P039E-I043V-A047V-L080V-E087D-S099R-S126A-P127E-S128G-N242D
54) P039E-I043V-A047V-T056Y-L080V-E087D-S099R-S126A-P127E-S128G-N242D
55) P039E-I043V-A047V-T056Y-L080V-E087D-S099R-N114Q-P127E-S128G-N242D
56) P039E-I043V-A047V-P054T-T056Y-L080V-E087D-S099R-P127E-S128G-N242D
57) P039E-E087D-S099R-S126A-P127E-S128G
58) P039E-I043V-A047V-T056Y-L080V-E087D-S099R-P127E-S128G-N242D
59) P039E-I043V-A047V-P054T-T056Y-L080V-E087D-S099R-N114Q-S126A-S128G-N242D
60) P039E-S099R-S126A-P127E-S128G
61) P039E-I043V-A047V-P054T-T056Y-L080V-E087D-S099R-N114Q-S126A-P127E-S128G-N242D
62) P039E-I043V-A047V-P054T-T056Y-L080V-E087D-S099R-S126A-P127E-S128G-N242D
63) P039E-I043V-A047V-T056Y-L080V-E087D-S099R-N114Q-S126A-S128G-N242D
64) P039E-I043V-A047V-T056Y-S099R-S126A-P127E-S128G
65) P039E-I043V-A047V-P054T-T056Y-S099R-N114Q-S126A-P127E-S128G
66) P039E-A047V-P054T-T056Y-L080V-E087D-S099R-S126A-P127E-S128G-N242D
67) P039E-I043V-A047V-P054T-T056Y-L080V-E087D-S099R-S126A-S128G-N242D
68) P039E-I043V-A047V-P054T-T056Y-L080V-E087D-N114Q-S126A-P127E-S128G-N242D
69) P039E-I043V-A047V-T056Y-L080V-E087D-S126A-P127E-S128G-N242D
70) P039E-A047V-T056Y-L080V-E087D-S099R-N114Q-S126A-P127E-S128G-N242D
71) P039E-S099R-S126A-P127E-S128G

72) P039E-A047V-P054T-T056Y-L080V-E087D-S099R-N114Q-S126A-P127E-S128G-N242D
73) P039E-I043V-A047V-T056Y-L080V-E087D-N114Q-S126A-P127E-S128G-N242D
74) P039E-A047V-T056Y-L080V-E087D-S099R-S126A-P127E-S128G-N242D
75) P039E-S099R-S126A-P127E-S128G-Q256E
76) P039E-S099R-S126A-P127E-S128G-N242D
77) P039E-S099R-S126A-P127E-S128G-Q200L
78) P039E-I043V-A047V-P054T-T056Y-S099R-N114Q-S126A-P127E-S128G-N242D
79) P039E-I043V-A047V-P054T-T056Y-S099R-S126A-P127E-S128G-N242D
80) P039E-N074D-L080V-S099R-S126A-P127E-S128G
81) P039E-I043V-A047V-P054T-T056Y-E087D-S099R-S126A-P127E-S128G-N242D
82) P039E-I043V-A047V-T056Y-E087D-S099R-N114Q-S126A-P127E-S128G-N242D
83) P039E-I043V-A047V
84) P039E-I043V-A047V-N242D
85) P039E-P054T-N074D-S099R-S126A-P127E-S128G
86) P039E-A047V-N074D-S099R-S126A-P127E-S128G
87) P039E-I043V-A047V-P054T-T056Y-E087D-S099R-N114Q-S126A-P127E-S128G-N242D
88) P039E-N074D-S099R-N114Q-S126A-P127E-S128G
89) P039E-N074D-S099R-S126A-P127E-S128G
90) P039E-I043V-A047V-T056Y-E087D-S099R-S126A-P127E-S128G-N242D
91) P039E-N074D-E087D-S099R-S126A-P127E-S128G
92) P039E-I043V-N074D-S099R-S126A-P127E-S128G
93) P039E-T056Y-N074D-S099R-S126A-P127E-S128G
94) P039E-N074D-S099R-S126A-P127E-S128G-N242D

Other preferred variants for use in the composition of the invention are selected from the group consisting of variants having at least 90%, more preferably at least 92% identity with the amino acid sequence SEQ ID NO:2 and comprising substitutions (using the SEQ ID NO:2 numbering) selected from the group consisting of:
(i) P39E-I43V-A47V-T56Y-L80V-E87D-S99R-N114Q-S126D-P127S-S128A-N242D;
(ii) P39E-I43V-A47V-T56Y-L80V-E87D-N114Q-S126G-P127T-S128E-N242D;
(iii) P39E-I43V-A47V-T56Y-L80V-E87D-S99R-N114Q-P127A-S128C-N242D;
(iv) P39E-I43V-A47V-P54T-T56Y-L80V-E87D-S99E-N114Q-S126T-P127D-S128A-N242D;
(v) P39E-I43V-A47V-P54T-T56Y-L80V-E87D-S99R-N114Q-S126V-P127A-S128T-N242D;
(vi) P39E-I43V-A47V-P54T-T56Y-L80V-E87D-S99R-N114Q-S128E-N242D;
(vii) P39E-I43V-A47V-T56Y-L80V-E87D-S99E-N114Q-P127E-S128G-N242D;
(viii) P39E-I43V-A47V-P54T-T56Y-L80V-E87D-S99R-N114Q-S126T-P127E-S128A-N242D;
(ix) P39E-I43V-A47V-T56Y-L80V-E87D-S128E-N242D;
(x) P39E-I43V-A47V-P54T-T56Y-L80V-E87D-S99R-N114Q-S126G-P127E-S128D-N242D;
(xi) P39E-I43V-A47V-T56Y-L80V-E87D-S99R-N114Q-P127D-S128E-N242D;
(xii) P39E-I43V-A47V-T56Y-L80V-E87D-S99R-N114Q-S126T-P127E-S128E-N242D;
(xiii) P39E-I43V-A47V-P54T-T56Y-L80V-E87D-S99R-N114Q-P127G-S128P-N242D;
(xiv) P39E-I43V-A47V-P54T-T56Y-L80V-E87D-S99R-N114Q-P127G-S128E-N242D; and/or
(xv) P39E-I43V-A47V-P54T-T56Y-L80V-E87D-S99E-N114Q-S126T-P127D-S128A-N242D.

In other embodiments, the protease is a variant having at least 90% identity with a sequence selected from the group consisting of SEQ ID NO:3, SEQ ID NO:4, SEQ ID NO:5, SEQ ID NO:6, SEQ ID NO:7; SEQ ID NO:8, SEQ ID NO:9 and SEQ ID NO:10 and the variant comprises at least one substitution selected from the group consisting of:
X54T;
X80V, R, Y;
X126A, D, G, V, E, K, I;
X127E, S, T, A, G, C; and
X128E, C, T, D, P, G, L, Y, N.

Preferably, the variant has a sequence having at least 90% identity with a sequence selected from the group consisting of SEQ ID NO:3, SEQ ID NO:4, SEQ ID NO:5, SEQ ID NO:6, SEQ ID NO:7; SEQ ID NO:8, SEQ ID NO:9 and SEQ ID NO:10 and the variant comprises at least one amino acid substitution selected from the group consisting of X54T, X80V, X126A, X127E and X128G.

Preferred variants have a sequence having at least 90% identity with a sequence selected from the group consisting of SEQ ID NO:3, SEQ ID NO:4, SEQ ID NO:5, SEQ ID NO:6, SEQ ID NO:7; SEQ ID NO:8, SEQ ID NO:9 and SEQ ID NO:10. The substitutions listed above (1)-94) and (i) to (xv)) for SEQ ID NO:2 applies mutatis mutandis to SEQ ID NO:3, SEQ ID NO:4, SEQ ID NO:5, SEQ ID NO:6, SEQ ID NO:7; SEQ ID NO:8, SEQ ID NO:9 and SEQ ID NO:10, regardless of the amino acid residue present in these sequences at the positions listed for SEQ ID NO:2. It is understood that SEQ ID NO:3, SEQ ID NO:4, SEQ ID NO:5, SEQ ID NO:6, SEQ ID NO:7; SEQ ID NO:8, SEQ ID NO:9 and SEQ ID NO:10 might not have the same amino acid residues as SEQ ID. NO:2 in the same positions, but the variants comprise the same substitutions.

For example:
T056Y-S099R-S126A-P127E-S128G with respect to SEQ ID No:2 becomes X056Y-X099R-X126A-X127E-X128G with respect to any of SEQ ID NO:3, SEQ ID NO:4, SEQ ID NO:5, SEQ ID NO:6, SEQ ID NO:7; SEQ ID NO:8, SEQ ID NO:9 and SEQ ID NO:10.

The protease of the first aspect of the invention performs very well in phosphate-free compositions even when the compositions are used in soft water.

Protease of the Second Aspect of the Invention

The variants of the present invention have at least 90%, more preferably at least 92% identity with the protease of SEQ ID NO: 1 or with the protease of SEQ ID NO: 2 or with one of the proteases of sequences ID NO: 3-10.

The protease of the invention can be selected from:
a) a variant having at least 90%, preferably at least 92% identity with the amino acid sequence of SEQ ID NO:1 and comprising at least one amino acid substitution (using the SEQ ID NO:1 numbering) selected from the group consisting of S39E, S99R, S126A-D127E-F128G, N242D and mixtures thereof; and
b) a variant having at least 90%, preferably at least 92% identity with the amino acid sequence of SEQ ID NO:2 and comprising at least one amino acid substitution (using the SEQ ID NO:2 numbering) selected from the group consisting of X39E, X126A-X127E-X128G, X242D and mixtures thereof.

Preferably, the variant comprises at least two, more preferably at least three amino acid substitutions (using the SEQ ID NO:1 numbering) selected from the group consisting of S39E, S99R, S126A-D127E-F128G and N242D, and preferably the variant comprises the following substitutions S39E, S99R, S126A-D127E-F128G and N242D.

Preferably, the variant further comprises at least one amino acid substitution (using the SEQ ID NO:1 numbering) selected from P54T, X114Q and X114C, preferably T114Q.

Preferably, the variant further comprises at least one and more preferably at least two and more preferably three amino acid substitution(s) (using the SEQ ID NO:1 numbering) selected from the group consisting of N74D; I80V, R, Y; N85S, C, D, I, K; E87D, C and M211L.

Preferably, the variant comprises at least 90% identity with the amino acid sequence of SEQ ID NO:1 and said variant further comprises at least one substitution (using the SEQ ID NO:1 numbering), preferably at least two substitutions and specially at least three substitutions selected from the group consisting of T3V, T9R, A15T, V66A, N74D, N85R, N97NE, N97AD, N97D/G, S99G/M, S101A, V102E/I, N116V/R, S126L, D127Q, F128A, G157S, Y161A, R164S, T188P, V199I, Q200C/E/I/K/T/V/W/L, Y203W, N212D, M216S/F, Q239R and T249R.

Especially preferred variants for use in the composition of the invention are selected from the group consisting of variants having at least 90%, more preferably at least 92% identity with the amino acid sequence SEQ ID:1 and comprising substitutions (using the SEQ ID NO:1 numbering) selected from the group consisting of:

1) T056Y-S099R-S126A-D127E-F128G
2) S039E-I080V-S099R-S126A-D127E-F128G-M211L
3) S039E-P054T-S099R-S126A-D127E-F128G-M211L
4) S039E-I043V-S099R-S126A-D127E-F128G-M211L
5) S039E-N042R-S099R-S126A-D127E-F128G
6) S039E-I080V-S099R-S126A-D127E-F128G
7) S039E-S099R-S126A-D127E-F128G-M211L
8) S039E-N085S-S099R-S126A-D127E-F128G-M211L
9) S039E-T056Y-S099R-S126A-D127E-F128G-M211L
10) S039E-A047V-S099R-S126A-D127E-F128G-M211L
11) S039E-S099R-S126A-D127E-F128G-Y203W
12) A037T-S039E-S099R-S126A-D127E-F128G-M211L
13) S039E-S099R-S126A-D127E-F128G-V199I
14) A037T-S039E-I043V-A047V-P054T-T056Y-I080V-N085S-E087D-S099R-T114Q-S126A-D127E-F128G
15) S039E-I043V-A047V-P054T-T056Y-I080V-N085S-E087D-S099R-S126A-D127E-F128G-N242D
16) A037T-S039E-I043V-A047V-T056Y-I080V-N085S-E087D-S099R-T114Q-S126A-D127E-F128G
17) A037T-S039E-I043V-A047V-P054T-T056Y-I080V-N085S-E087D-S099R-S126A-D127E-F128G
18) S039E-I043V-S099R-S126A-D127E-F128G
19) S039E-S099R-S126A-D127E-F128G-N253D
20) T009E-S039E-S099R-S126A-D127E-F128G
21) S039E-S099R-S126A-D127E-F128G-S255W
22) A037T-S039E-I043V-A047V-P054T-T056Y-I080V-N085S-S099R-S126A-D127E-F128G-N242D
23) A037T-S039E-I043V-P054T-T056Y-I080V-N085S-E087D-S099R-S126A-D127E-F128G-N242D
24) S039E-I043V-A047V-T056Y-I080V-N085S-E087D-S099R-S126A-D127E-F128G-N242D
25) S039E-I043V-A047V-T056Y-I080V-N085S-E087D-S099R-T114Q-S126A-D127E-F128G-N242D
26) S039E-T056Y-S099R-S126A-D127E-F128G
27) A037T-S039E-I043V-A047V-T056Y-I080V-N085S-E087D-S099R-S126A-D127E-F128G
28) A037T-S039E-I043V-P054T-T056Y-I080V-N085S-E087D-S099R-T114Q-S126A-D127E-F128G-N242D
29) A037T-S039E-I043V-T056Y-I080V-N085S-E087D-S099R-T114Q-S126A-D127E-F128G-N242D
30) A037T-S039E-I043V-A047V-I080V-N085S-E087D-S099R-T114Q-S126A-D127E-F128G-N242D
31) A037T-S039E-I043V-A047V-P054T-I080V-N085S-E087D-S099R-S126A-D127E-F128G-N242D
32) A037T-S039E-I043V-A047V-T056Y-I080V-N085S-E087D-S099R-S126A-D127E-N242D
33) A037T-S039E-I043V-T056Y-I080V-N085S-E087D-S099R-S126A-D127E-F128G-N242D
34) A037T-S039E-I043V-A047V-T056Y-I080V-N085S-E087D-S099R-T114Q-S126A-D127E-N242D
35) S039E-N085S-S099R-S126A-D127E-F128G
36) A037T-S039E-I043V-A047V-P054T-I080V-N085S-E087D-S099R-T114Q-S126A-D127E-F128G-N242D
37) A037T-S039E-I043V-A047V-P054T-T056Y-I080V-N085S-S099R-T114Q-S126A-D127E-F128G-N242D
38) A037T-S039E-I043V-A047V-P054T-T056Y-I080V-N085S-E087D-S099R-T114Q-S126A-D127E-N242D
39) A037T-S039E-I043V-A047V-P054T-T056Y-I080V-N085S-E087D-S126A-D127E-F128G-N242D
40) A037T-S039E-I043V-A047V-T056Y-I080V-N085S-E087D-S099R-S126A-F128G-N242D
41) A037T-S039E-I043V-A047V-T056Y-I080V-E087D-S099R-T114Q-S126A-D127E-F128G-N242D
42) S039E-S099R-T114Q-S126A-D127E-F128G
43) A037T-S039E-I043V-A047V-P054T-T056Y-I080V-N085S-E087D-S099R-S126A-D127E-N242D
44) A037T-S039E-I043V-A047V-T056Y-I080V-N085S-E087D-S099R-S126A-D127E-F128G-N242D
45) A037T-S039E-I043V-A047V-P054T-T056Y-I080V-N085S-E087D-S099R-T114Q-D127E-F128G-N242D
46) A037T-S039E-I043V-A047V-T056Y-I080V-N085S-S099R-T114Q-S126A-D127E-F128G-N242D
47) S039E-A047V-S099R-S126A-D127E-F128G
48) A037T-S039E-I043V-A047V-T056Y-I080V-N085S-S099R-S126A-D127E-F128G-N242D
49) A037T-S039E-I043V-A047V-T056Y-S099R-T114Q-S126A-D127E-F128G
50) A037T-S039E-I043V-A047V-P054T-T056Y-I080V-E087D-S099R-S126A-D127E-F128G-N242D
51) S039E-P054T-S099R-S126A-D127E-F128G
52) A037T-S039E-I043V-A047V-P054T-T056Y-I080V-N085S-E087D-S099R-T114Q-S126A-D127E-F128G-N242D
53) A037T-S039E-I043V-A047V-I080V-N085S-E087D-S099R-S126A-D127E-F128G-N242D
54) A037T-S039E-I043V-A047V-T056Y-I080V-E087D-S099R-S126A-D127E-F128G-N242D
55) A037T-S039E-I043V-A047V-T056Y-I080V-N085S-E087D-S099R-T114Q-D127E-F128G-N242D
56) A037T-S039E-I043V-A047V-P054T-T056Y-I080V-N085S-E087D-S099R-D127E-F128G-N242D
57) S039E-E087D-S099R-S126A-D127E-F128G
58) A037T-S039E-I043V-A047V-T056Y-I080V-N085S-E087D-S099R-D127E-F128G-N242D
59) A037T-S039E-I043V-A047V-P054T-T056Y-I080V-N085S-E087D-S099R-T114Q-S126A-F128G-N242D
60) A037T-S039E-S099R-S126A-D127E-F128G
61) A037T-S039E-I043V-A047V-P054T-T056Y-I080V-E087D-S099R-T114Q-S126A-D127E-F128G-N242D
62) A037T-S039E-I043V-A047V-P054T-T056Y-I080V-N085S-E087D-S099R-S126A-D127E-F128G-N242D
63) A037T-S039E-I043V-A047V-T056Y-I080V-N085S-E087D-S099R-T114Q-S126A-F128G-N242D
64) A037T-S039E-I043V-A047V-T056Y-S099R-S126A-D127E-F128G
65) A037T-S039E-I043V-A047V-P054T-T056Y-S099R-T114Q-S126A-D127E-F128G

66) A037T-S039E-A047V-P054T-T056Y-I080V-N085S-E087D-S099R-S126A-D127E-F128G-N242D
67) A037T-S039E-I043V-A047V-P054T-T056Y-I080V-N085S-E087D-S099R-S126A-F128G-N242D
68) A037T-S039E-I043V-A047V-P054T-T056Y-I080V-N085S-E087D-T114Q-S126A-D127E-F128G-N242D
69) A037T-S039E-I043V-A047V-T056Y-I080V-N085S-E087D-S126A-D127E-F128G-N242D
70) A037T-S039E-A047V-T056Y-I080V-N085S-E087D-S099R-T114Q-S126A-D127E-F128G-N242D
71) S039E-S099R-S126A-D127E-F128G
72) A037T-S039E-A047V-P054T-T056Y-I080V-N085S-E087D-S099R-T114Q-S126A-D127E-F128G-N242D
73) A037T-S039E-I043V-A047V-T056Y-I080V-N085S-E087D-T114Q-S126A-D127E-F128G-N242D
74) A037T-S039E-A047V-T056Y-I080V-N085S-E087D-S099R-S126A-D127E-F128G-N242D
75) S039E-S099R-S126A-D127E-F128G-Q256E
76) S039E-S099R-S126A-D127E-F128G-N242D
77) S039E-S099R-S126A-D127E-F128G-Q200L
78) A037T-S039E-I043V-A047V-P054T-T056Y-S099R-T114Q-S126A-D127E-F128G-N242D
79) A037T-S039E-I043V-A047V-P054T-T056Y-S099R-S126A-D127E-F128G-N242D
80) S039E-N074D-I080V-S099R-S126A-D127E-F128G
81) A037T-S039E-I043V-A047V-P054T-T056Y-N085S-E087D-S099R-S126A-D127E-F128G-N242D
82) A037T-S039E-I043V-A047V-T056Y-N085S-E087D-S099R-T114Q-S126A-D127E-F128G-N242D
83) A037T-S039E-I043V-A047V
84) A037T-S039E-I043V-A047V-N242D
85) S039E-P054T-N074D-S099R-S126A-D127E-F128G
86) S039E-A047V-N074D-S099R-S126A-D127E-F128G
87) A037T-S039E-I043V-A047V-P054T-T056Y-N085S-E087D-S099R-T114Q-S126A-D127E-F128G-N242D
88) S039E-N074D-S099R-T114Q-S126A-D127E-F128G
89) S039E-N074D-N085S-S099R-S126A-D127E-F128G
90) A037T-S039E-I043V-A047V-T056Y-N085S-E087D-S099R-S126A-D127E-F128G-N242D
91) S039E-N074D-E087D-S099R-S126A-D127E-F128G
92) S039E-I043V-N074D-S099R-S126A-D127E-F128G
93) S039E-T056Y-N074D-S099R-S126A-D127E-F128G
94) S039E-N074D-S099R-S126A-D127E-F128G-N242D

Especially preferred variants for use in the composition of the invention are selected from the group consisting of variants having at least 90%, more preferably at least 92% identity with the amino acid sequence SEQ ID:1 and comprising substitutions (using the SEQ ID NO:1 numbering) selected from the group consisting of:

(o) A37T-S39E-I43V-A47V-T56Y-I80V-N85S-E87D-S99R-T114Q-S126D-D127S-F128A-N242D;
(p) A37T-S39E-I43V-A47V-T56Y-I80V-N85S-E87D-T114Q-S126G-D127T-F128E-N242D;
(q) A37T-S39E-I43V-A47V-T56Y-I80V-N85S-E87D-S99R-T114Q-D127A-F128C-N242D;
(r) A37T-S39E-I43V-A47V-P54T-T56Y-I80V-N85S-E87D-S99E-T114Q-S126T-F128T-N242D;
(s) A37T-S39E-I43V-A47V-P54T-T56Y-I80V-N85S-E87D-S99R-T114Q-S126V-D127A-F128T-N242D;
(t) A37T-S39E-I43V-A47V-P54T-T56Y-I80V-N85S-E87D-S99R-T114Q-F128E-N242D;
(u) A37T-S39E-I43V-A47V-T56Y-I80V-N85S-E87D-S99R-T114Q-D127E-F128G-N242D;
(v) A37T-S39E-I43V-A47V-P54T-T56Y-I80V-N85S-E87D-S99R-T114Q-S126T-D127E-F128A-N242D;
(w) A37T-S39E-I43V-A47V-T56Y-I80V-N85S-E87D-T114Q-D127P-F128E-N242D;
(x) A37T-S39E-I43V-A47V-P54T-T56Y-I80V-N85S-E87D-S99R-T114Q-S126G-D127E-F128D-N242D;
(y) A37T-S39E-I43V-A47V-T56Y-I80V-N85S-E87D-S99R-T114Q-F128E-N242D;
(z) A37T-S39E-I43V-A47V-T56Y-I80V-N85S-E87D-S99R-T114Q-S126T-D127E-F128E-N242D;
(aa) A37T-S39E-I43V-A47V-P54T-T56Y-I80V-N85S-E87D-S99R-T114Q-D127G-F128P-N242D; and
(bb) A37T-S39E-I43V-A47V-P54T-T56Y-I80V-N85S-E87D-S99R-T114Q-D127G-F128E-N242D.

Preferably, the variant has at least 90% identity with SEQ ID NO:2 and comprises at least two, more preferably at least three amino acid substitutions (using the SEQ ID NO:2 numbering) selected from the group consisting of X39E, X126A-X127E-X128G and X242D, preferably P39E, S126A-P127E-S128G and N242D and preferably the variant comprises the following substitutions P39E, S126A-P127E-S128G and N242D.

Preferably, the variant further comprises at least one amino acid substitution (using the SEQ ID NO:2 numbering) selected from P54T, N114Q and N114C.

Preferably, the variant further comprises at least one and more preferably at least two and more preferably three amino acid substitution(s) (using the SEQ ID NO:2 numbering) selected from the group consisting of N74D; L80V, R, Y; S85S, C, D, I, K; and E87D, C.

Preferably, the variant has at least 90% identity with the amino acid sequence of a parent protease said parent protease having the amino acid sequence of SEQ ID NO:2 and said variant further comprises at least one substitution (using the SEQ ID NO:2 numbering), preferably at least two substitutions and specially at least three substitutions selected from the group consisting of S3V, S9R, A15T, V66A, N74D, S85N/R, S97SE, S97AD, S97D/G, S99G/M, S101A, V102E/I, G116V/R, S126F, P127Q, S128A, G157S, Y161A, R164S, A188P, V199I, Q200C/E/I/K/T/V/W/L, Y203W, N212D, M216S/F, Q239R and T249R.

Especially preferred variants for use in the composition of the invention are selected from the group consisting of variants having at least 90%, more preferably at least 92% identity with the amino acid sequence SEQ ID NO:2 and comprising substitutions (using the SEQ ID NO:2 numbering) selected from the group consisting of:

1) T056Y-S099R-S126A-P127E-S128G
2) P039E-L080V-S099R-S126A-P127E-S128G-M211L
3) P039E-P054T-S099R-S126A-P127E-S128G-M211L
4) P039E-I043V-S099R-S126A-P127E-S128G-M211L
5) P039E-N042R-S099R-S126A-P127E-S128G
6) P039E-L080V-S099R-S126A-P127E-S128G
7) P039E-S099R-S126A-P127E-S128G-M211L
8) P039E-S099R-S126A-P127E-S128G-M211L
9) P039E-T056Y-S099R-S126A-P127E-S128G-M211L
10) P039E-A047V-S099R-S126A-P127E-S128G-M211L
11) P039E-S099R-S126A-P127E-S128G-Y203W
12) P039E-S099R-S126A-P127E-S128G-M211L
13) P039E-S099R-S126A-P127E-S128G-V199I
14) P039E-I043V-A047V-P054T-T056Y-L080V-E087D-S099R-N114Q-S126A-P127E-S128G
15) P039E-I043V-A047V-P054T-T056Y-L080V-E087D-S099R-S126A-P127E-S128G-N242D

16) P039E-I043V-A047V-T056Y-L080V-E087D-S099R-N114Q-S126A-P127E-S128G
17) P039E-I043V-A047V-P054T-T056Y-L080V-E087D-S099R-S126A-P127E-S128G
18) P039E-I043V-S099R-S126A-P127E-S128G
19) P039E-S099R-S126A-P127E-S128G-N253D
20) T009E-P039E-S099R-S126A-P127E-S128G
21) P039E-S099R-S126A-P127E-S128G-S255W
22) P039E-I043V-A047V-P054T-T056Y-L080V-S099R-S126A-P127E-S128G-N242D
23) P039E-I043V-P054T-T056Y-L080V-E087D-S099R-S126A-P127E-S128G-N242D
24) P039E-I043V-A047V-T056Y-L080V-E087D-S099R-S126A-P127E-S128G-N242D
25) P039E-I043V-A047V-T056Y-L080V-E087D-S099R-N114Q-S126A-P127E-S128G-N242D
26) P039E-T056Y-S099R-S126A-P127E-S128G
27) P039E-I043V-A047V-T056Y-L080V-E087D-S099R-S126A-P127E-S128G
28) P039E-I043V-P054T-T056Y-L080V-E087D-S099R-N114Q-S126A-P127E-S128G-N242D
29) P039E-I043V-T056Y-L080V-E087D-S099R-N114Q-S126A-P127E-S128G-N242D
30) P039E-I043V-A047V-L080V-E087D-S099R-N114Q-S126A-P127E-S128G-N242D
31) P039E-I043V-A047V-P054T-L080V-E087D-S099R-S126A-P127E-S128G-N242D
32) P039E-I043V-A047V-T056Y-L080V-E087D-S099R-S126A-P127E-N242D
33) P039E-I043V-T056Y-L080V-E087D-S099R-S126A-P127E-S128G-N242D
34) P039E-I043V-A047V-T056Y-L080V-E087D-S099R-N114Q-S126A-P127E-N242D
35) P039E-S099R-S126A-P127E-S128G
36) P039E-I043V-A047V-P054T-L080V-E087D-S099R-N114Q-S126A-P127E-S128G-N242D
37) P039E-I043V-A047V-P054T-T056Y-L080V-S099R-N114Q-S126A-P127E-S128G-N242D
38) P039E-I043V-A047V-P054T-T056Y-L080V-E087D-S099R-N114Q-S126A-P127E-N242D
39) P039E-I043V-A047V-P054T-T056Y-L080V-E087D-S126A-P127E-S128G-N242D
40) P039E-I043V-A047V-T056Y-L080V-E087D-S099R-S126A-S128G-N242D
41) P039E-I043V-A047V-T056Y-L080V-E087D-S099R-N114Q-S126A-P127E-S128G-N242D
42) P039E-S099R-N114Q-S126A-P127E-S128G
43) P039E-I043V-A047V-P054T-T056Y-L080V-E087D-S099R-S126A-P127E-N242D
44) P039E-I043V-A047V-T056Y-L080V-E087D-S099R-S126A-P127E-S128G-N242D
45) P039E-I043V-A047V-P054T-T056Y-L080V-E087D-S099R-N114Q-P127E-S128G-N242D
46) P039E-I043V-A047V-T056Y-L080V-S099R-N114Q-S126A-P127E-S128G-N242D
47) P039E-A047V-S099R-S126A-P127E-S128G
48) P039E-I043V-A047V-T056Y-L080V-S099R-S126A-P127E-S128G-N242D
49) P039E-I043V-A047V-T056Y-S099R-N114Q-S126A-P127E-S128G
50) P039E-I043V-A047V-P054T-T056Y-L080V-E087D-S099R-S126A-P127E-S128G-N242D
51) P039E-P054T-S099R-S126A-P127E-S128G
52) P039E-I043V-A047V-P054T-T056Y-L080V-E087D-S099R-N114Q-S126A-P127E-S128G-N242D
53) P039E-I043V-A047V-L080V-E087D-S126A-P127E-S128G-N242D
54) P039E-I043V-A047V-T056Y-L080V-E087D-S099R-S126A-P127E-S128G-N242D
55) P039E-I043V-A047V-T056Y-L080V-E087D-S099R-N114Q-P127E-S128G-N242D
56) P039E-I043V-A047V-P054T-T056Y-L080V-E087D-S099R-P127E-S128G-N242D
57) P039E-E087D-S099R-S126A-P127E-S128G
58) P039E-I043V-A047V-T056Y-L080V-E087D-S099R-P127E-S128G-N242D
59) P039E-I043V-A047V-P054T-T056Y-L080V-E087D-S099R-N114Q-S126A-S128G-N242D
60) P039E-S099R-S126A-P127E-S128G
61) P039E-I043V-A047V-P054T-T056Y-L080V-E087D-S099R-N114Q-S126A-P127E-S128G-N242D
62) P039E-I043V-A047V-P054T-T056Y-L080V-E087D-S099R-S126A-P127E-S128G-N242D
63) P039E-I043V-A047V-T056Y-L080V-E087D-S099R-N114Q-S126A-S128G-N242D
64) P039E-I043V-A047V-T056Y-S099R-S126A-P127E-S128G
65) P039E-I043V-A047V-P054T-T056Y-S099R-N114Q-S126A-P127E-S128G
66) P039E-A047V-P054T-T056Y-L080V-E087D-S099R-S126A-P127E-S128G-N242D
67) P039E-I043V-A047V-P054T-T056Y-L080V-E087D-S099R-S126A-S128G-N242D
68) P039E-I043V-A047V-P054T-T056Y-L080V-E087D-N114Q-S126A-P127E-S128G-N242D
69) P039E-I043V-A047V-T056Y-L080V-E087D-S126A-P127E-S128G-N242D
70) P039E-A047V-T056Y-L080V-E087D-S099R-N114Q-S126A-P127E-S128G-N242D
71) P039E-S099R-S126A-P127E-S128G
72) P039E-A047V-P054T-T056Y-L080V-E087D-S099R-N114Q-S126A-P127E-S128G-N242D
73) P039E-I043V-A047V-T056Y-L080V-E087D-N114Q-S126A-P127E-S128G-N242D
74) P039E-A047V-T056Y-L080V-E087D-S099R-S126A-P127E-S128G-N242D
75) P039E-S099R-S126A-P127E-S128G-Q256E
76) P039E-S099R-S126A-P127E-S128G-N242D
77) P039E-S099R-S126A-P127E-S128G-Q200L
78) P039E-I043V-A047V-P054T-T056Y-S099R-N114Q-S126A-P127E-S128G-N242D
79) P039E-I043V-A047V-P054T-T056Y-S099R-S126A-P127E-S128G-N242D
80) P039E-N074D-L080V-S099R-S126A-P127E-S128G
81) P039E-I043V-A047V-P054T-T056Y-E087D-S099R-S126A-P127E-S128G-N242D
82) P039E-I043V-A047V-T056Y-E087D-S099R-N114Q-S126A-P127E-S128G-N242D
83) P039E-I043V-A047V
84) P039E-I043V-A047V-N242D
85) P039E-P054T-N074D-S099R-S126A-P127E-S128G
86) P039E-A047V-N074D-S099R-S126A-P127E-S128G
87) P039E-I043V-A047V-P054T-T056Y-E087D-S099R-N114Q-S126A-P127E-S128G-N242D
88) P039E-N074D-S099R-N114Q-S126A-P127E-S128G
89) P039E-N074D-S099R-S126A-P127E-S128G
90) P039E-I043V-A047V-T056Y-E087D-S099R-S126A-P127E-S128G-N242D
91) P039E-N074D-E087D-S099R-S126A-P127E-S128G
92) P039E-I043V-N074D-S099R-S126A-P127E-S128G
93) P039E-T056Y-N074D-S099R-S126A-P127E-S128G
94) P039E-N074D-S099R-S126A-P127E-S128G-N242D

Especially preferred variants for use in the composition of the invention are selected from the group consisting of variants having at least 90%, more preferably at least 92% identity with the amino acid sequence SEQ ID NO:2 and comprising substitutions (using the SEQ ID NO:2 numbering) selected from the group consisting of:

(i) P39E-I43V-A47V-T56Y-L80V-E87D-S99R-N114Q-S126D-P127S-S128A-N242D;
(ii) P39E-I43V-A47V-T56Y-L80V-E87D-N114Q-S126G-P127T-S128E-N242D;
(iii) P39E-I43V-A47V-T56Y-L80V-E87D-S99R-N114Q-P127A-S128C-N242D;
(iv) P39E-I43V-A47V-P54T-T56Y-L80V-E87D-S99E-N114Q-S126T-P127D-S128A-N242D;
(v) P39E-I43V-A47V-P54T-T56Y-L80V-E87D-S99R-N114Q-S126V-P127A-S128T-N242D;
(vi) P39E-I43V-A47V-P54T-T56Y-L80V-E87D-S99R-N114Q-S128E-N242D;
(vii) P39E-I43V-A47V-T56Y-L80V-E87D-S99E-N114Q-P127E-S128G-N242D;
(viii) P39E-I43V-A47V-P54T-T56Y-L80V-E87D-S99R-N114Q-S126T-P127E-S128A-N242D;
(ix) P39E-I43V-A47V-T56Y-L80V-E87D-S128E-N242D;
(x) P39E-I43V-A47V-P54T-T56Y-L80V-E87D-S99R-N114Q-S126G-P127E-S128D-N242D;
(xi) P39E-I43V-A47V-T56Y-L80V-E87D-S99R-N114Q-P127D-S128E-N242D;
(xii) P39E-I43V-A47V-T56Y-L80V-E87D-S99R-N114Q-S126T-P127E-S128E-N242D;
(xiii) P39E-I43V-A47V-P54T-T56Y-L80V-E87D-S99R-N114Q-S126A-P127E-S128G-N242D;
(xiv) P39E-I43V-A47V-P54T-T56Y-L80V-E87D-S99R-N114Q-P127G-S128P-N242D;
(xv) P39E-I43V-A47V-P54T-T56Y-L80V-E87D-S99R-N114Q-P127G-S128E-N242D;
(xvi) P39E-I43V-A47V-P54T-T56Y-L80V-E87D-S99R-N114Q-S126A-P127D-S128G-N242D; and/or
(xvii) P39E-I43V-A47V-P54T-T56Y-L80V-E87D-S99E-N114Q-S126T-P127D-S128A-N242D Preferably, the variant has 90% identity with a sequence selected from the group consisting of SEQ ID NO:3, SEQ ID NO:4, SEQ ID NO:5, SEQ ID NO:6, SEQ ID NO:7; SEQ ID NO:8, SEQ ID NO:9 and SEQ ID NO:10 and comprises at least two, more preferably at least three amino acid substitutions (using the SEQ ID NO:2 numbering) selected from the group consisting of X39E, X126A-X127E-X128G and X242D, and preferably the variant comprises the following substitutions X39E, X126A-X127E-X128G and X242D.

Preferably, the variant further comprises at least one amino acid substitution (using the SEQ ID NO:2 numbering) selected from X54T, X114Q and X114C.

Preferably, the variant further comprises at least one and more preferably at least two and more preferably three amino acid substitution(s) (using the SEQ ID NO:2 numbering) selected from the group consisting of X74D; X80V, R, Y; X85S, C, D, I, K; and X87D, C.

Preferred variants have a sequence having at least 90% identity with a sequence selected from the group consisting of SEQ ID NO:3, SEQ ID NO:4, SEQ ID NO:5, SEQ ID NO:6, SEQ ID NO:7; SEQ ID NO:8, SEQ ID NO:9 and SEQ ID NO:10. The substitutions listed above (1)-94) and (i) to (xvii)) for SEQ ID NO:2 applies mutatis mutandis to SEQ ID NO:3, SEQ ID NO:4 SEQ ID NO:5, SEQ ID NO:6, SEQ ID NO:7; SEQ ID NO:8, SEQ ID NO:9 and SEQ ID NO:10, regardless of the amino acid residue present in these sequences at the positions listed for SEQ ID2. It is understood that SEQ ID NO:3, SEQ ID NO:4, SEQ ID NO:5, SEQ ID NO:6, SEQ ID NO:7; SEQ ID NO:8, SEQ ID NO:9 and SEQ ID NO:10 might not have the same amino acid residues as SEQ ID. NO:2 in these positions, but the variants comprise the same substitutions.

For example:

T056Y-S099R-S126A-P127E-S128G with respect to SEQ ID No:2 becomes X056Y-X099R-X126A-X127E-X128G with respect to any of SEQ ID NO:3, SEQ ID NO:4, SEQ ID NO:5, SEQ ID NO:6, SEQ ID NO:7; SEQ ID NO:8, SEQ ID NO:9 and SEQ ID NO:10.

The protease of the invention performs very well in phosphate-free compositions even when the compositions are used in soft water.

Preferred levels of protease in the composition of the invention include from about 0.04 to about 5 mg, more preferably from about 0.05 to about 2 mg of active protease per gram of the composition.

Automatic Dishwashing Cleaning Composition

The automatic dishwashing cleaning composition can be in any physical form. It can be a loose powder, a gel or presented in unit dose form. Preferably it is in unit dose form, unit dose forms include pressed tablets and water-soluble packs. The automatic dishwashing cleaning composition of the invention is preferably presented in unit-dose form and it can be in any physical form including solid, liquid and gel form. The composition of the invention is very well suited to be presented in the form of a multi-compartment pack, more in particular a multi-compartment pack comprising compartments with compositions in different physical forms, for example a compartment comprising a composition in solid form and another compartment comprising a composition in liquid form. The composition is preferably enveloped by a water-soluble film such as polyvinyl alcohol. Especially preferred are compositions in unit dose form wrapped in a polyvinyl alcohol film having a thickness of less than 100 µm, preferably from 20 to 90 µm. The detergent composition of the invention weighs from about 8 to about 25 grams, preferably from about 10 to about 20 grams. This weight range fits comfortably in a dishwasher dispenser. Even though this range amounts to a low amount of detergent, the detergent has been formulated in a way that provides all the benefits mentioned herein above.

The composition is preferably phosphate free. By "phosphate-free" is herein understood that the composition comprises less than 1%, preferably less than 0.1% by weight of the composition of phosphate.

The composition of the invention is phosphate-free and comprises a complexing agent system.

Complexing Agent System

For the purpose of this invention, a "complexing agent" is a compound capable of binding polyvalent ions such as calcium, magnesium, lead, copper, zinc, cadmium, mercury, manganese, iron, aluminium and other cationic polyvalent ions to form a water-soluble complex. The complexing agent has a logarithmic stability constant ([log K]) for Ca2+ of at least 3. The stability constant, log K, is measured in a solution of ionic strength of 0.1, at a temperature of 25° C. The composition of the invention comprises from 10% to 50% by weight of the composition of a complexing agent system. Preferably, the composition comprises a complexing agent selected from the group consisting of citric acid, methyl glycine diacetic acid (MGDA), glutamic-N,N-diacetic acid (GLDA), iminodisuccinic acid (IDS), carboxy methyl inulin, L-Aspartic acid N, N-diacetic acid tetrasodium salt (ASDA) and mixtures thereof. For the purpose of this invention, the term "acid", when referring to complexing agents, includes acid and salts thereof.

In a preferred embodiment, the composition comprises from 15% to 40% by weight of the invention of MGDA, more preferably the tri-sodium salt of MGDA. Compositions comprising this high level of MGDA perform well in soft and/or hard water and also in long and/or hot cycles.

In a preferred embodiment, the composition comprises from 15% to 28% by weight of the invention of citric acid, more preferably sodium citrate. Compositions comprising citric acid perform well in soft water.

In a preferred embodiment, the complexing agent system comprises citric acid and MGDA preferably in a weight ratio of from about 0.5:1 to about 5:1, more preferably from about 0.5:1 to about 2.5:1.

Dispersant Polymer

Preferably, the composition of the invention comprises a dispersant polymer. A dispersant polymer can be used in any suitable amount from about 0.1 to about 20%, preferably from 0.2 to about 15%, more preferably from 0.3 to % by weight of the composition.

The dispersant polymer is capable to suspend calcium or calcium carbonate in an automatic dishwashing process.

The dispersant polymer has a calcium binding capacity within the range between 30 to 250 mg of Ca/g of dispersant polymer, preferably between 35 to 200 mg of Ca/g of dispersant polymer, more preferably 40 to 150 mg of Ca/g of dispersant polymer at 25° C. In order to determine if a polymer is a dispersant polymer within the meaning of the invention, the following calcium binding-capacity determination is conducted in accordance with the following instructions:

Calcium Binding Capacity Test Method

The calcium binding capacity referred to herein is determined via titration using a pH/ion meter, such as the Mettler Toledo SevenMulti™ bench top meter and a PerfectION™ comb Ca combination electrode. To measure the binding capacity a heating and stirring device suitable for beakers or tergotometer pots is set to 25° C., and the ion electrode with meter are calibrated according to the manufacturer's instructions. The standard concentrations for the electrode calibration should bracket the test concentration and should be measured at 25° C. A stock solution of 1000 mg/g of Ca is prepared by adding 3.67 g of $CaCl_2 \cdot 2H_2O$ into 1 L of deionised water, then dilutions are carried out to prepare three working solutions of 100 mL each, respectively comprising 100 mg/g, 10 mg/g, and 1 mg/g concentrations of Calcium. The 100 mg Ca/g working solution is used as the initial concentration during the titration, which is conducted at 25° C. The ionic strength of each working solution is adjusted by adding 2.5 g/L of NaCl to each. The 100 mL of 100 mg Ca/g working solution is heated and stirred until it reaches 25° C. The initial reading of Calcium ion concentration is conducted at when the solution reaches 25° C. using the ion electrode. Then the test polymer is added incrementally to the calcium working solution (at 0.01 g/L intervals) and measured after 5 minutes of agitation following each incremental addition. The titration is stopped when the solution reaches 1 mg/g of Calcium. The titration procedure is repeated using the remaining two calcium concentration working solutions. The binding capacity of the test polymer is calculated as the linear slope of the calcium concentrations measured against the grams/L of test polymer that was added.

The dispersant polymer preferably bears a negative net charge when dissolved in an aqueous solution with a pH greater than 6.

The dispersant polymer can bear also sulfonated carboxylic esters or amides, in order to increase the negative charge at lower pH and improve their dispersing properties in hard water. The preferred dispersant polymers are sulfonated/carboxylated polymers, i.e., polymer comprising both sulfonated and carboxylated monomers.

Preferably, the dispersant polymers are sulfonated derivatives of polycarboxylic acids and may comprise two, three, four or more different monomer units. The preferred copolymers contain:

At least one structural unit derived from a carboxylic acid monomer having the general formula (III):

wherein $R_1$ to $R_3$ are independently selected from hydrogen, methyl, linear or branched saturated alkyl groups having from 2 to 12 carbon atoms, linear or branched mono or polyunsaturated alkenyl groups having from 2 to 12 carbon atoms, alkyl or alkenyl groups as aforementioned substituted with —$NH2$ or —OH, or —COOH, or $COOR_4$, where $R_4$ is selected from hydrogen, alkali metal, or a linear or branched, saturated or unsaturated alkyl or alkenyl group with 2 to 12 carbons;

Preferred carboxylic acid monomers include one or more of the following: acrylic acid, maleic acid, maleic anhydride, itaconic acid, citraconic acid, 2-phenylacrylic acid, cinnamic acid, crotonic acid, fumaric acid, methacrylic acid, 2-ethylacrylic acid, methylenemalonic acid, or sorbic acid. Acrylic and methacrylic acids being more preferred.

Optionally, one or more structural units derived from at least one nonionic monomer having the general formula (IV):

Wherein $R_5$ to $R_7$ are independently selected from hydrogen, methyl, phenyl or hydroxyalkyl groups containing 1 to 6 carbon atoms, and can be part of a cyclic structure, X is an optionally present spacer group which is selected from —$CH_2$—, —COO—, —CONH— or —$CONR_8$—, and R8 is selected from linear or branched, saturated alkyl radicals having 1 to 22 carbon atoms or unsaturated, preferably aromatic, radicals having from 6 to 22 carbon atoms.

Preferred non-ionic monomers include one or more of the following: butene, isobutene, pentene, 2-methylpent-1-ene, 3-methylpent-1-ene, 2,4,4-trimethylpent-1-ene, 2,4,4-trimethylpent-2-ene, cyclopentene, methylcyclopentene, 2-methyl-3-methyl-cyclopentene, hexene, 2,3-dimethylhex-1-ene, 2,4-dimethylhex-1-ene, 2,5-dimethylhex-1-ene, 3,5-dimethylhex-1-ene, 4,4-dimethylhex-1-ene, cyclohexene, methylcyclohexene, cycloheptene, alpha olefins having 10 or more carbon atoms such as, dec-1-ene, dodec-1-ene, hexadec-1-ene, octadec-1-ene and docos-1-ene, preferred aromatic monomers are styrene, alpha methylstyrene, 3-methylstyrene, 4-dodecylstyrene, 2-ethyl-4-bezylstyrene, 4-cyclohexylstyrene, 4-propylstyrol, 1-vinylnaphtalene, 2-vinylnaphtalene; preferred carboxylic ester monomers are methyl (meth)acrylate, ethyl (meth)acrylate, propyl (meth) acrylate, t-butyl (meth)acrylate, pentyl (meth)acrylate, hexyl (meth)acrylate, 2-ethylhexyl (meth)acrylate, octyl (meth) acrylate, lauryl (meth)acrylate, stearyl (meth)acrylate and behenyl (meth)acrylate; preferred amides are N-methyl acrylamide, N-ethyl acrylamide, N-t-butyl acrylamide, N-2-ethylhexyl acrylamide, N-octyl acrylamide, N-lauryl acrylamide, N-stearyl acrylamide, N-behenyl acrylamide.

and at least one structural unit derived from at least one sulfonic acid monomer having the general formula (V) and (VI):

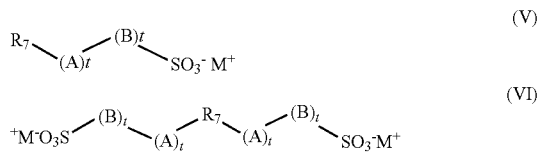

wherein R7 is a group comprising at least one sp2 bond, A is O, N, P, S, an amido or ester linkage, B is a mono- or polycyclic aromatic group or an aliphatic group, each t is independently 0 or 1, and M+ is a cation. In one aspect, R7 is a C2 to C6 alkene. In another aspect, R7 is ethene, butene or propene.

Preferred sulfonated monomers include one or more of the following: 1-acrylamido-1-propanesulfonic acid, 2-acrylamido-2-propanesulfonic acid, 2-acrylamido-2-methyl-1-propanesulfonic acid, 2-methacrylamido-2-methyl-1-propanesulfonic acid, 3-methacrylamido-2-hydroxy-propanesulfonic acid, allylsulfonic acid, methallylsulfonic acid, allyloxybenzenesulfonic acid, methallyloxybenzene-sulfonic acid, 2-hydroxy-3-(2-propenyloxy) propanesulfonic acid, 2-methyl-2-propen-1-sulfonic acid, styrenesulfonic acid, vinylsulfonic acid, 3-sulfopropyl, 3-sulfo-propylmeth-acrylate, sulfomethacrylamide, sulfomethylmethacrylamide and mixtures of said acids or their water-soluble salts.

Preferably, the polymer comprises the following levels of monomers: from about 40 to about 90%, preferably from about 60 to about 90% by weight of the polymer of one or more carboxylic acid monomer; from about 5 to about 50%, preferably from about 10 to about 40% by weight of the polymer of one or more sulfonic acid monomer; and optionally from about 1% to about 30%, preferably from about 2 to about 20% by weight of the polymer of one or more non-ionic monomer. An especially preferred polymer comprises about 70% to about 80% by weight of the polymer of at least one carboxylic acid monomer and from about 20% to about 30% by weight of the polymer of at least one sulfonic acid monomer.

In the polymers, all or some of the carboxylic or sulfonic acid groups can be present in neutralized form, i.e. the acidic hydrogen atom of the carboxylic and/or sulfonic acid group in some or all acid groups can be replaced with metal ions, preferably alkali metal ions and in particular with sodium ions.

The carboxylic acid is preferably (meth)acrylic acid. The sulfonic acid monomer is preferably 2-acrylamido-2-propanesulfonic acid (AMPS).

Preferred commercial available polymers include: Alcosperse 240, Aquatreat AR 540 and Aquatreat MPS supplied by Alco Chemical; Acumer 3100, Acumer 2000, Acusol 587G and Acusol 588G supplied by Rohm & Haas; Goodrich K-798, K-775 and K-797 supplied by BF Goodrich; and ACP 1042 supplied by ISP technologies Inc. Particularly preferred polymers are Acusol 587G and Acusol 588G supplied by Rohm & Haas.

Suitable dispersant polymers include anionic carboxylic polymer of low molecular weight. They can be homopolymers or copolymers with a weight average molecular weight of less than or equal to about 200,000 g/mol, or less than or equal to about 75,000 g/mol, or less than or equal to about 50,000 g/mol, or from about 3,000 to about 50,000 g/mol, preferably from about 5,000 to about 45,000 g/mol. The dispersant polymer may be a low molecular weight homopolymer of polyacrylate, with an average molecular weight of from 1,000 to 20,000, particularly from 2,000 to 10,000, and particularly preferably from 3,000 to 5,000.

The dispersant polymer may be a copolymer of acrylic with methacrylic acid, acrylic and/or methacrylic with maleic acid, and acrylic and/or methacrylic with fumaric acid, with a molecular weight of less than 70,000. Their molecular weight ranges from 2,000 to 80,000 and more preferably from 20,000 to 50,000 and in particular 30,000 to 40,000 g/mol. and a ratio of (meth)acrylate to maleate or fumarate segments of from 30:1 to 1:2.

The dispersant polymer may be a copolymer of acrylamide and acrylate having a molecular weight of from 3,000 to 100,000, alternatively from 4,000 to 20,000, and an acrylamide content of less than 50%, alternatively less than 20%, by weight of the dispersant polymer can also be used. Alternatively, such dispersant polymer may have a molecular weight of from 4,000 to 20,000 and an acrylamide content of from 0% to 15%, by weight of the polymer.

Dispersant polymers suitable herein also include itaconic acid homopolymers and copolymers. Alternatively, the dispersant polymer can be selected from the group consisting of alkoxylated polyalkyleneimines, alkoxylated polycarboxy-lates, polyethylene glycols, styrene co-polymers, cellulose sulfate esters, carboxylated polysaccharides, amphiphilic graft copolymers and mixtures thereof.

Bleach

The composition of the invention preferably comprises from about 10 to about 20%, more preferably from about 12 to about 18% of bleach, preferably percarbonate, by weight of the composition.

Inorganic and organic bleaches are suitable for use herein. Inorganic bleaches include perhydrate salts such as perborate, percarbonate, perphosphate, persulfate and persilicate salts. The inorganic perhydrate salts are normally the alkali metal salts. The inorganic perhydrate salt may be included as the crystalline solid without additional protection. Alternatively, the salt can be coated. Suitable coatings include sodium sulphate, sodium carbonate, sodium silicate and mixtures thereof. Said coatings can be applied as a mixture applied to the surface or sequentially in layers.

Alkali metal percarbonates, particularly sodium percarbonate is the preferred bleach for use herein. The percarbonate is most preferably incorporated into the products in a coated form which provides in-product stability.

Potassium peroxymonopersulfate is another inorganic perhydrate salt of utility herein.

Typical organic bleaches are organic peroxyacids, especially dodecanediperoxoic acid, tetradecanediperoxoic acid, and hexadecanediperoxoic acid. Mono- and diperazelaic acid, mono- and diperbrassylic acid are also suitable herein. Diacyl and Tetraacylperoxides, for instance dibenzoyl peroxide and dilauroyl peroxide, are other organic peroxides that can be used in the context of this invention.

Further typical organic bleaches include the peroxyacids, particular examples being the alkylperoxy acids and the arylperoxy acids. Preferred representatives are (a) peroxybenzoic acid and its ring-substituted derivatives, such as alkylperoxybenzoic acids, but also peroxy-α-naphthoic acid and magnesium monoperphthalate, (b) the aliphatic or substituted aliphatic peroxy acids, such as peroxylauric acid, peroxystearic acid, ε-phthalimidoperoxycaproic acid[phthaloiminoperoxyhexanoic acid (PAP)], o-carboxybenzamidoperoxycaproic acid, N-nonenylamidoperadipic acid and N-nonenylamidopersuccinates, and (c) aliphatic and aralilphatic peroxydicarboxylic acids, such as 1,12-diperoxycarboxylic acid, 1,9-diperoxyazelaic acid, diperoxysebacic acid, diperoxybrassylic acid, the diperoxyphthalic acids, 2-decyldiperoxybutane-1,4-dioic acid, N,N-terephthaloyldi (6-aminopercaproic acid).

Bleach Activators

Bleach activators are typically organic peracid precursors that enhance the bleaching action in the course of cleaning at temperatures of 60° C. and below. Bleach activators suitable for use herein include compounds which, under perhydrolysis conditions, give aliphatic peroxoycarboxylic acids having preferably from 1 to 12 carbon atoms, in particular from 2 to 10 carbon atoms, and/or optionally substituted perbenzoic acid. Suitable substances bear O-acyl and/or N-acyl groups of the number of carbon atoms specified and/or optionally substituted benzoyl groups. Preference is given to polyacylated alkylenediamines, in particular tetraacetylethylenediamine (TAED), acylated triazine derivatives, in particular 1,5-diacetyl-2,4-dioxohexahydro-1,3,5-triazine (DADHT), acylated glycolurils, in particular tetraacetylglycoluril (TAGU), N-acylimides, in particular N-nonanoylsuccinimide (NOSI), acylated phenolsulfonates, in particular n-nonanoyl- or isononanoyloxybenzenesulfonate (n- or iso-NOBS), decanoyloxybenzoic acid (DOBA), carboxylic anhydrides, in particular phthalic anhydride, acylated polyhydric alcohols, in particular triacetin, ethylene glycol diacetate and 2,5-diacetoxy-2,5-dihydrofuran and also triethylacetyl citrate (TEAC). If present the composition of the invention comprises from 0.01 to 5, preferably from 0.2 to 2% by weight of the composition of bleach activator, preferably TAED.

Bleach Catalyst

The composition herein preferably contains a bleach catalyst, preferably a metal containing bleach catalyst. More preferably the metal containing bleach catalyst is a transition metal containing bleach catalyst, especially a manganese or cobalt-containing bleach catalyst.

Bleach catalysts preferred for use herein include manganese triazacyclononane and related complexes; Co, Cu, Mn and Fe bispyridylamine and related complexes; and pentamine acetate cobalt(III) and related complexes. Especially preferred bleach catalyst for use herein are 1,4,7-trimethyl-1,4,7-triazacyclononane (Me-TACN) and 1,2, 4,7-tetramethyl-1,4,7-triazacyclononane (Me/Me-TACN).

Preferably the composition of the invention comprises from 0.005 to 0.5, more preferably from 0.005 to 0.075% of bleach catalyst by weight of the composition. Preferably the bleach catalyst is a manganese bleach catalyst.

Inorganic Builder

The composition of the invention preferably comprises an inorganic builder. Suitable inorganic builders are selected from the group consisting of carbonate, silicate and mixtures thereof. Especially preferred for use herein is sodium carbonate. Preferably the composition of the invention comprises from 5 to 60%, more preferably from 10 to 50% and especially from 15 to 45% of sodium carbonate by weight of the composition.

Surfactant

Surfactants suitable for use herein include non-ionic surfactants, preferably the compositions are free of any other surfactants. Traditionally, non-ionic surfactants have been used in automatic dishwashing for surface modification purposes in particular for sheeting to avoid filming and spotting and to improve shine. It has been found that non-ionic surfactants can also contribute to prevent redeposition of soils.

Preferably the composition of the invention comprises a non-ionic surfactant or a non-ionic surfactant system, more preferably the non-ionic surfactant or a non-ionic surfactant system has a phase inversion temperature, as measured at a concentration of 1% in distilled water, between 40 and 70° C., preferably between 45 and 65° C. By a "non-ionic surfactant system" is meant herein a mixture of two or more non-ionic surfactants. Preferred for use herein are non-ionic surfactant systems. They seem to have improved cleaning and finishing properties and better stability in product than single non-ionic surfactants.

Phase inversion temperature is the temperature below which a surfactant, or a mixture thereof, partitions preferentially into the water phase as oil-swollen micelles and above which it partitions preferentially into the oil phase as water swollen inverted micelles. Phase inversion temperature can be determined visually by identifying at which temperature cloudiness occurs.

The phase inversion temperature of a non-ionic surfactant or system can be determined as follows: a solution containing 1% of the corresponding surfactant or mixture by weight of the solution in distilled water is prepared. The solution is stirred gently before phase inversion temperature analysis to ensure that the process occurs in chemical equilibrium. The phase inversion temperature is taken in a thermostable bath by immersing the solutions in 75 mm sealed glass test tube. To ensure the absence of leakage, the test tube is weighed before and after phase inversion temperature measurement. The temperature is gradually increased at a rate of less than 1° C. per minute, until the temperature reaches a few degrees below the pre-estimated phase inversion temperature. Phase inversion temperature is determined visually at the first sign of turbidity. Suitable nonionic surfactants include: i) ethoxylated non-ionic surfactants prepared by the reaction of a monohydroxy alkanol or alkyphenol with 6 to 20 carbon atoms with preferably at least 12 moles particularly preferred at least 16 moles, and still more preferred at least 20 moles of ethylene oxide per mole of alcohol or alkylphenol; ii) alcohol alkoxylated surfactants having a from 6 to 20 carbon atoms and at least one ethoxy and propoxy group. Preferred for use herein are mixtures of surfactants i) and ii).

Another suitable non-ionic surfactants are epoxy-capped poly(oxyalkylated) alcohols represented by the formula:

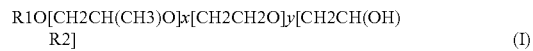

R1O[CH2CH(CH3)O]x[CH2CH2O]y[CH2CH(OH)R2]     (I)

wherein R1 is a linear or branched, aliphatic hydrocarbon radical having from 4 to 18 carbon atoms; R2 is a linear or branched aliphatic hydrocarbon radical having from 2 to 26 carbon atoms; x is an integer having an average value of from 0.5 to 1.5, more preferably about 1; and y is an integer having a value of at least 15, more preferably at least 20.

Preferably, the surfactant of formula I, at least about 10 carbon atoms in the terminal epoxide unit [CH2CH(OH)R2]. Suitable surfactants of formula I, according to the present invention, are Olin Corporation's POLY-TERGENT® SLF-18B nonionic surfactants, as described, for example, in WO 94/22800, published Oct. 13, 1994 by Olin Corporation.

Enzymes
Other Proteases

The composition of the invention can comprise a protease in addition to the protease of the invention. A mixture of two or more proteases can contribute to an enhanced cleaning across a broader temperature, cycle duration, and/or substrate range, and provide superior shine benefits, especially when used in conjunction with an anti-redeposition agent and/or a sulfonated polymer.

Suitable proteases for use in combination with the variant proteases of the invention include metalloproteases and serine proteases, including neutral or alkaline microbial serine proteases, such as subtilisins (EC 3.4.21.62). Suitable proteases include those of animal, vegetable or microbial origin. In one aspect, such suitable protease may be of microbial origin. The suitable proteases include chemically or genetically modified mutants of the aforementioned suitable proteases. In one aspect, the suitable protease may be a serine protease, such as an alkaline microbial protease or/and a trypsin-type protease. Examples of suitable neutral or alkaline proteases include:

(a) subtilisins (EC 3.4.21.62), especially those derived from *Bacillus*, such as *Bacillus* sp., *B. lentus*, *B. alkalophilus*, *B. subtilis*, *B. amyloliquefaciens*, *B. pumilus*, *B. gibsonii*, and *B. akibaii* described in WO2004067737, WO2015091989, WO2015091990, WO2015024739, WO2015143360, U.S. Pat. No. 6,312,936 B1, U.S. Pat. Nos. 5,679,630, 4,760,025, DE102006022216A1, DE102006022224A1, WO2015-089447, WO2015089441, WO2016066756, WO2016-066757, WO2016069557, WO2016069563, WO2016-069569.

(b) trypsin-type or chymotrypsin-type proteases, such as trypsin (e.g., of porcine or bovine origin), including the *Fusarium* protease described in WO 89/06270 and the chymotrypsin proteases derived from *Cellumonas* described in WO 05/052161 and WO 05/052146.

(c) metalloproteases, especially those derived from *Bacillus amyloliquefaciens* described in WO07/044993A2; from *Bacillus, Brevibacillus, Thermoactinomyces, Geobacillus, Paenibacillus, Lysinibacillus* or *Streptomyces* spp. Described in WO2014194032, WO2014194054 and WO2014194117; from *Kribella alluminosa* described in WO2015193488; and from *Streptomyces* and *Lysobacter* described in WO2016075078.

(d) protease having at least 90% identity to the subtilase from *Bacillus* sp. TY145, NCIMB 40339, described in WO92/17577 (Novozymes A/S), including the variants of this *Bacillus* sp TY145 subtilase described in WO2015024739, and WO2016066757.

Especially preferred additional proteases for the detergent of the invention are polypeptides demonstrating at least 90%, preferably at least 95%, more preferably at least 98%, even more preferably at least 99% and especially 100% identity with the wild-type enzyme from *Bacillus lentus*, comprising mutations in one or more, preferably two or more and more preferably three or more of the following positions, using the BPN' numbering system and amino acid abbreviations as illustrated in WO00/37627, which is incorporated herein by reference: V68A, N76D, N87S, S99D, S99SD, S99A, S101G, S101M, S103A, V104N/I, G118V, G118R, S128L, P129Q, S130A, Y167A, R170S, A194P, V205I, Q206L/D/E, Y209W and/or M222S.

Most preferably the additional protease is selected from the group of proteases comprising the below mutations (BPN' numbering system) versus either the PB92 wild-type (SEQ ID NO:2 in WO 08/010925) or the subtilisin 309 wild-type (sequence as per PB92 backbone, except comprising a natural variation of N87S).

(i) G118V+S128L+P129Q+S130A
(ii) S101M+G118V+S128L+P129Q+S130A
(iii) N76D+N87R+G118R+S128L+P129Q+S130A+S188D+N248R
(iv) N76D+N87R+G118R+S128L+P129Q+S130A+S188D+V244R
(v) N76D+N87R+G118R+S128L+P129Q+S130A
(vi) V68A+N87S+S101G+V104N
(vii) S99AD Suitable commercially available additional protease enzymes include those sold under the trade names Alcalase®, Savinase®, Primase®, Durazym®, Polarzyme®, Kannase®, Liquanase®, Liquanase Ultra®, Savinase Ultra®, Ovozyme®, Neutrase®, Everlase®, Coronase®, Blaze®, Blaze Ultra® and Esperase® by Novozymes A/S (Denmark); those sold under the tradename Maxatase®, Maxacal®, Maxapem®, Properase®, Purafect®, Purafect Prime®, Purafect Ox®, FN3®, FN4®, Excellase®, Ultimase® and Purafect OXP® by Dupont; those sold under the tradename Opticlean® and Optimase® by Solvay Enzymes; and those available from Henkel/Kemira, namely BLAP (sequence shown in FIG. 29 of U.S. Pat. No. 5,352,604 with the following mutations S99D+S101 R+S103A+V104I+G159S, hereinafter referred to as BLAP), BLAP R (BLAP with S3T+V4I+V199M+V205I+L217D), BLAP X (BLAP with S3T+V4I+V205I) and BLAP F49 (BLAP with S3T+V4I+A194P+V199M+V205I+L217D); and KAP (*Bacillus alkalophilus* subtilisin with mutations A230V+S256G+S259N) from Kao.

Especially preferred for use herein in combination with the variant protease of the invention are commercial proteases selected from the group consisting of Properase®, Blaze®, Ultimase®, Everlase®, Savinase®, Excellase®, Blaze Ultra®, BLAP and BLAP variants.

Preferred levels of protease in the product of the invention include from about 0.05 to about 10, more preferably from about 0.5 to about 7 and especially from about 1 to about 6 mg of active protease/g of composition.

Amylases

Preferably the composition of the invention may comprise an amylase. Suitable alpha-amylases include those of bacterial or fungal origin. Chemically or genetically modified mutants (variants) are included. A preferred alkaline alpha-amylase is derived from a strain of *Bacillus*, such as *Bacillus licheniformis, Bacillus amyloliquefaciens, Bacillus stearothermophilus, Bacillus subtilis*, or other *Bacillus* sp., such as *Bacillus* sp. NCBI 12289, NCBI 12512, NCBI 12513, DSM 9375 (U.S. Pat. No. 7,153,818) DSM 12368, DSMZ no. 12649, KSM AP1378 (WO 97/00324), KSM K36 or KSM K38 (EP 1,022,334). Preferred amylases include:

(a) variants described in WO 96/23873, WO00/60060, WO06/002643 and WO2017/192657, especially the variants with one or more substitutions in the following positions versus the AA560 enzyme listed as SEQ ID NO. 12 in WO06/002643:
26, 30, 33, 82, 37, 106, 118, 128, 133, 149, 150, 160, 178, 182, 186, 193, 202, 214, 231, 246, 256, 257, 258, 269, 270, 272, 283, 295, 296, 298, 299, 303, 304, 305, 311, 314, 315, 318, 319, 339, 345, 361, 378, 383, 419, 421, 437, 441, 444, 445, 446, 447, 450, 461, 471, 482, 484, preferably that also contain the deletions of D183* and G184*.

(b) variants exhibiting at least 90% identity with SEQ ID No. 4 in WO06/002643, the wild-type enzyme from *Bacillus* SP722, especially variants with deletions in the 183 and 184 positions and variants described in WO 00/60060, WO2011/100410 and WO2013/003659 which are incorporated herein by reference.

(c) variants exhibiting at least 95% identity with the wild-type enzyme from *Bacillus* sp. 707 (SEQ ID NO:7 in U.S. Pat. No. 6,093,562), especially those comprising one or more of the following mutations M202, M208, S255, R172, and/or M261. Preferably said amylase comprises one or more of M202L, M202V, M202S, M202T, M202I, M202Q, M202W, S255N and/or R172Q. Particularly preferred are those comprising the M202L or M202T mutations.

(d) variants described in WO 09/149130, preferably those exhibiting at least 90% identity with SEQ ID NO: 1 or SEQ ID NO:2 in WO 09/149130, the wild-type enzyme from *Geobacillus Stearophermophilus* or a truncated version thereof.

(e) variants exhibiting at least 89% identity with SEQ ID NO:1 in WO2016091688, especially those comprising deletions at positions H183+G184 and additionally one or more mutations at positions 405, 421, 422 and/or 428.

(f) variants exhibiting at least 60% amino acid sequence identity with the "PcuAmyl α-amylase" from *Paenibacillus curdlanolyticus* YK9 (SEQ ID NO:3 in WO2014099523).

(g) variants exhibiting at least 60% amino acid sequence identity with the "CspAmy2 amylase" from *Cytophaga* sp. (SEQ ID NO:1 in WO2014164777).

(h) variants exhibiting at least 85% identity with AmyE from *Bacillus subtilis* (SEQ ID NO:1 in WO2009149271).

(i) variants exhibiting at least 90% identity with the wild-type amylase from *Bacillus* sp. KSM-K38 with accession number AB051102.

(j) variants exhibiting at least 80% identity with the mature amino acid sequence of AAI10 from *Bacillus* sp (SEQ ID NO:7 in WO2016180748)

(k) variants exhibiting at least 80% identity with the mature amino acid sequence of *Alicyclobacillus* sp. amylase (SEQ ID NO:8 in WO2016180748)

Preferably the amylase is an engineered enzyme, wherein one or more of the amino acids prone to bleach oxidation have been substituted by an amino acid less prone to oxidation. In particular it is preferred that methionine residues are substituted with any other amino acid. In particular it is preferred that the methionine most prone to oxidation is substituted. Preferably the methionine in a position equivalent to 202 in the AA560 enzyme listed as SEQ ID NO. 12 in WO06/002643 is substituted. Preferably, the methionine at this position is substituted with threonine or leucine, preferably leucine.

Suitable commercially available alpha-amylases include DURAMYL®, LIQUEZYME®, TERMAMYL®, TERMAMYL ULTRA®, NATALASE®, SUPRAMYL®, STAINZYME®, STAINZYME PLUS®, FUNGAMYL®, ATLANTIC®, INTENSA® and BAN® (Novozymes A/S, Bagsvaerd, Denmark), KEMZYM® AT 9000 Biozym Biotech Trading GmbH Wehlistrasse 27b A-1200 Wien Austria, RAPIDASE®, PURASTAR®, ENZYSIZE®, OPTISIZE HT PLUS®, POWERASE®, PREFERENZ S® series (including PREFERENZ S1000® and PREFERENZ S2000® and PURASTAR OXAM® (DuPont., Palo Alto, California) and KAM® (Kao, 14-10 Nihonbashi Kayabacho, 1-chome, Chuo-ku Tokyo 103-8210, Japan). In one aspect, suitable amylases include ATLANTIC®, STAINZYME®, POWERASE®, INTENSA® and STAINZYME PLUS® and mixtures thereof.

Preferably, the product of the invention comprises at least 0.01 mg, preferably from about 0.05 to about 10, more preferably from about 0.1 to about 6, especially from about 0.2 to about 5 mg of active amylase/g of composition.

Preferably, the protease and/or amylase of the composition of the invention are in the form of granulates, the granulates comprise more than 29% of sodium sulfate by weight of the granulate and/or the sodium sulfate and the active enzyme (protease and/or amylase) are in a weight ratio of between 3:1 and 100:1 or preferably between 4:1 and 30:1 or more preferably between 5:1 and 20:1.

Crystal Growth Inhibitor

Crystal growth inhibitors are materials that can bind to calcium carbonate crystals and prevent further growth of species such as aragonite and calcite.

Examples of effective crystal growth inhibitors include phosphonates, polyphosphonates, inulin derivatives, polyitaconic acid homopolymers and cyclic polycarboxylates.

Suitable crystal growth inhibitors may be selected from the group comprising HEDP (1-hydroxyethylidene 1,1-diphosphonic acid), carboxymethylinulin (CMI), tricarballylic acid and cyclic carboxylates. For the purposes of this invention the term carboxylate covers both the anionic form and the protonated carboxylic acid form.

Cyclic carboxylates contain at least two, preferably three or preferably at least four carboxylate groups and the cyclic structure is based on either a mono- or bi-cyclic alkane or a heterocycle. Suitable cyclic structures include cyclopropane, cyclobutane, cyclohexane or cyclopentane or cycloheptane, bicyclo-heptane or bicyclo-octane and/or tetrhaydrofuran. One preferred crystal growth inhibitor is cyclopentane tetracarboxylate.

Cyclic carboxylates having at least 75%, preferably 100% of the carboxylate groups on the same side, or in the "cis" position of the 3D-structure of the cycle are preferred for use herein.

It is preferred that the two carboxylate groups, which are on the same side of the cycle are in directly neighbouring or "ortho" positions.

Preferred crystal growth inhibitors include HEDP, tricarballylic acid, tetrahydrofurantetracarboxylic acid (THFTCA) and cyclopentanetetracarboxylic acid (CPTCA). The THFTCA is preferably in the 2c,3t,4t,5c-configuration, and the CPTCA in the cis,cis,cis,cis-configuration. Especially preferred crystal growth inhibitor for use herein is HEDP.

Also preferred for use herein are partially decarboxylated polyitaconic acid homopolymers, preferably having a level of decarboxylation is in the range of 50 mole % to 90 mole %. Especially preferred polymer for use herein is Itaconix TSI® provided by Itaconix.

The crystal growth inhibitors are present preferably in a quantity from about 0.01 to about 10%, particularly from about 0.02 to about 5% and in particular, from 0.05 to 3% by weight of the composition.

Metal Care Agents

Metal care agents may prevent or reduce the tarnishing, corrosion or oxidation of metals, including aluminium, stainless steel and non-ferrous metals, such as silver and copper. Preferably the composition of the invention comprises from 0.1 to 5%, more preferably from 0.2 to 4% and especially from 0.3 to 3% by weight of the product of a metal care agent, preferably the metal care agent is benzo triazole (BTA).

Glass Care Agents

Glass care agents protect the appearance of glass items during the dishwashing process. Preferably the composition of the invention comprises from 0.1 to 5%, more preferably from 0.2 to 4% and specially from 0.3 to 3% by weight of the composition of a metal care agent, preferably the glass care agent is a zinc containing material, specially hydrozincite. Other suitable glass care agents are polyethyleneimine (PEI). A particularly preferred PEI is Lupasol® FG, supplied by BASF.

The automatic dishwashing composition of the invention preferably has a pH as measured in 1% weight/volume aqueous solution in distilled water at 20° C. of from about 9 to about 12, more preferably from about 10 to less than about 11.5 and especially from about 10.5 to about 11.5. The automatic dishwashing composition of the invention preferably has a reserve alkalinity of from about 10 to about 20, more preferably from about 12 to about 18 at a pH of 9.5 as measured in NaOH with 100 grams of product at 20° C.

A preferred automatic dishwashing composition of the invention comprises:
  i) from 10 to 20% by weight of the composition of bleach, preferably sodium percarbonate;
  ii) preferably a bleach activator, more preferably TAED;
  iii) amylases;
  iv) optionally but preferably from 5 to 50% by weight of the composition of an inorganic builder, preferably sodium carbonate;
  v) optionally but preferably from 2 to 10% by weight of the composition of a non-ionic surfactant;
  vi) optionally but preferably a bleach catalyst, more preferably a manganese bleach catalyst; and
  vii) other optional ingredients include: a crystal growth inhibitor, preferably HEDP, and glass care agents.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

EXAMPLES

Egg yolk removal by automatic dishwashing compositions comprising variant proteases were compared with the same compositions comprising the parent protease.

The compositions displayed in Table 1 were used. 3 g of each composition were dissolved in a litre of deionized water to produce a cleaning solution having a pH of 11. The corresponding protease was added to the cleaning solution at a level between 0.25-0.75 ppm.

TABLE 1

Automatic Dish Washing (ADW) Compositions

| | |
|---|---|
| Amylase | Stainzyme ® Plus supplied by Novozymes |
| TAED | Tetraacetylethylenediamine |
| MGDA | Three-sodium methyl glycine diacetate supplied by BASF |
| Bleach catalyst | MnTACN (Manganese 1,4,7-Triazacyclononane) |
| Sulfonated polymer | Acusol 588 supplied by Dow Chemicals |
| Lutensol TO7 | Nonionic surfactant supplied by BASF |

Cleaning Performance Method: Egg Yolk Cleaning Performance Using PAS-38.

The cleaning performance of the proteases variants listed in Table 2 was tested relative to the parent using Automatic Dishwashing Compositions A, B and C (see Table 1), as measured by the stain removal on egg yolk microswatches (PAS-38, Center for Testmaterials BV, Vlaardingen, Netherlands). The egg swatch stains were pre-sized to fit the microtiter plate (MTPs); standard 96 well plate. The stain removal of the PAS-38 egg swatches was measured post wash versus a reference.

The MTPs were filled prior to protease addition with 3 g/l of detergent and the detergent and deionized water.

After incubating the PAS-38 swatches for 30° C. min at 50° C., absorbance was read at 405 nm with a SpectraMax plate reader. Absorbance results were obtained by subtracting the value for a blank control (containing no protease) from each sample value (hereinafter "blank subtracted absorbance"). For each condition and variant, a performance index (PI) was calculated by dividing the blank subtracted absorbance by that of the parent protease at the same concentration. The value for the parent protease was determined from a standard curve of the parent protease which was included in the test and which was fitted to a Langmuir fit.

Protease Enzyme Activity Method 2: AAPF Assay

The protease activity of parent and subtilisin variants thereof was tested by measuring hydrolysis of N-suc-AAPF-pNA. The reagent solutions used for the AAPF hydrolysis assay were: 100 mM Tris/HCl pH 8.6, containing 0.005% TWEEN®-80 (Tris dilution buffer); 100 mM Tris buffer pH 8.6, containing 10 mM $CaCl_2$) and 0.005% TWEEN®-80 (Tris/Ca buffer); and 160 mM suc-AAPF-pNA in DMSO (suc-AAPF-pNA stock solution) (Sigma: S-7388). A substrate working solution was prepared by adding 1 mL suc-AAPF-pNA stock solution to 100 mL Tris/Ca buffer and mixed well. An enzyme sample was added to a MTP (Greiner 781101) containing 1 mg/suc-AAPF-pNA working solution and assayed for activity at 405 nm over 3 min with a SpectraMax plate reader in kinetic mode at room temperature (RT). The absorbance of a blank containing no protease was subtracted from each sample reading. The protease activity was expressed as mOD·$min^{-1}$.

Protease Enzyme Stability—Stability Assay

The stability of the variants described herein was measured by diluting the variants in stress buffer and measuring the proteolytic activity of the variants before and after a heat incubation step of 5 minutes at 56° C. using the AAPF assay described above. Stability was measured in Tris-EDTA (50 mM Tris pH 9; 5 mM EDTA; 0.005% Tween 80) buffered condition. % Residual activities were calculated by taking a ratio of the stressed to unstressed activity and multiplying by 100.

TABLE 1

Automatic Dishwashing Compositions

| Ingredients (active weight %) | ADW Formula A | ADW Formula B | ADW Formula C |
|---|---|---|---|
| Solid ingredients | | | |
| Sodium carbonate | 41.7 | 41.7 | 41.7 |
| Sodium sulphate | 0.00 | 1.68 | 2.03 |
| MGDA | 21.0 | 0.00 | 10.1 |
| Sodium citrate | 0.00 | 19.2 | 10.1 |
| TAED | 1.68 | 1.68 | 1.68 |
| Sodium percarbonate | 12.6 | 12.6 | 12.6 |
| Sulfonated polymer | 2.5 | 2.5 | 2.5 |
| Bleach catalyst | 1.2 | 1.2 | 1.2 |
| Amylase | 0.11 | 0.11 | 0.11 |
| Liquid ingredients | | | |
| Lutensol TO7 | 19.3 | 19.3 | 19.3 |

Protease Data Table 2

| Variants | Substitutions with respect to SEQ ID No: 1 | Stability TRIS-EDTA | PAS-38 stain Cleaning | | |
|---|---|---|---|---|---|
| | | | ADW formula A | ADW formula B | ADW formula C |
| SEQ ID No: 1 | none | 1 | 1.0 | 1.0 | 1.0 |
| WALBSP-07063 | T056Y-S099R-S126A-D127E-F128G | 9 | 1.7 | 2.2 | 2.6 |
| WALBSP-07078 | S039E-I080V-S099R-S126A-D127E-F128G-M211L | 21 | 2.2 | 3.5 | ND |
| WALBSP-07137 | S039E-P054T-S099R-S126A-D127E-F128G-M211L | 28 | 2.3 | 2.9 | ND |
| WALBSP-07117 | S039E-I043V-S099R-S126A-D127E-F128G-M211L | 28 | 2.3 | 3.0 | 3.7 |
| WALBSP-07119 | S039E-N042R-S099R-S126A-D127E-F128G | 28 | 2.3 | 3.1 | 3.9 |
| WALBSP-07052 | S039E-I080V-S099R-S126A-D127E-F128G | 29 | 2.1 | 2.5 | 2.8 |
| WALBSP-07097 | S039E-S099R-S126A-D127E-F128G-M211L | 29 | 2.4 | 2.6 | ND |
| WALBSP-07088 | S039E-N085S-S099R-S126A-D127E-F128G-M211L | 30 | 2.3 | 3.3 | 3.6 |
| WALBSP-07147 | S039E-T056Y-S099R-S126A-D127E-F128G-M211L | 31 | 2.0 | 3.5 | 3.8 |
| WALBSP-07127 | S039E-A047V-S099R-S126A-D127E-F128G-M211L | 31 | 2.2 | 2.6 | 3.9 |
| WALBSP-07149 | S039E-S099R-S126A-D127E-F128G-Y203W | 32 | 2.0 | 2.6 | ND |
| WALBSP-07107 | A037T-S039E-S099R-S126A-D127E-F128G-M211L | 32 | 2.3 | 3.3 | ND |
| WALBSP-07129 | S039E-S099R-S126A-D127E-F128G-V199I | 34 | 2.3 | 3.1 | 4.3 |
| WALBSP-07058 | A037T-S039E-I043V-A047V-P054T-T056Y-I080V-N085S-E087D-S099R-T114Q-S126A-D127E-F128G | 35 | 2.0 | 2.2 | 2.8 |
| WALBSP-07050 | S039E-I043V-A047V-P054T-T056Y-I080V-N085S-E087D-S099R-S126A-D127E-F128G-N242D | 35 | 2.0 | 2.4 | 2.9 |
| WALBSP-07040 | A037T-S039E-I043V-A047V-T056Y-I080V-N085S-E087D-S099R-T114Q-S126A-D127E-F128G | 36 | 2.0 | 2.7 | 3.1 |
| WALBSP-07014 | A037T-S039E-I043V-A047V-P054T-T056Y-I080V-N085S- | 37 | 3.6 | 3.4 | 3.9 |

| | Protease Data Table 2 | | | | |
|---|---|---|---|---|---|
| | Substitutions with | Stability | PAS-38 stain Cleaning | | |
| Variants | respect to SEQ ID No: 1 | TRIS-EDTA | ADW formula A | ADW formula B | ADW formula C |
| | E087D-S099R-S126A-D127E-F128G | | | | |
| WALBSP-07012 | S039E-I043V-S099R-S126A-D127E-F128G | 38 | 2.2 | 2.1 | 2.7 |
| WALBSP-07080 | S039E-S099R-S126A-D127E-F128G-N253D | 38 | 1.7 | 1.9 | ND |
| WALBSP-07109 | T009E-S039E-S099R-S126A-D127E-F128G | 38 | 2.1 | 3.0 | 3.4 |
| WALBSP-07090 | S039E-S099R-S126A-D127E-F128G-S255W | 38 | 2.4 | 2.9 | 3.8 |
| WALBSP-07041 | A037T-S039E-I043V-A047V-P054T-T056Y-I080V-N085S-S099R-S126A-D127E-F128G-N242D | 38 | 2.0 | 2.5 | 2.9 |
| WALBSP-07001 | A037T-S039E-I043V-P054T-T056Y-I080V-N085S-E087D-S099R-S126A-D127E-F128G-N242D | 38 | 1.9 | 2.4 | 3.0 |
| WALBSP-07024 | S039E-I043V-A047V-T056Y-I080V-N085S-E087D-S099R-S126A-D127E-F128G-N242D | 39 | 2.1 | 2.3 | 2.5 |
| WALBSP-07068 | S039E-I043V-A047V-T056Y-I080V-N085S-E087D-S099R-T114Q-S126A-D127E-F128G-N242D | 39 | 1.8 | 2.3 | 2.8 |
| WALBSP-07042 | S039E-T056Y-S099R-S126A-D127E-F128G | 39 | 2.1 | 2.3 | 2.6 |
| WALBSP-07065 | A037T-S039E-I043V-A047V-T056Y-I080V-N085S-E087D-S099R-S126A-D127E-F128G | 39 | 2.1 | 1.9 | 2.7 |
| WALBSP-07027 | A037T-S039E-I043V-P054T-T056Y-I080V-N085S-E087D-S099R-T114Q-S126A-D127E-F128G-N242D | 39 | 1.9 | 2.5 | 3.0 |
| WALBSP-07019 | A037T-S039E-I043V-T056Y-I080V-N085S-E087D-S099R-T114Q-S126A-D127E-F128G-N242D | 39 | 2.1 | 2.4 | 2.9 |
| WALBSP-07029 | A037T-S039E-I043V-A047V-I080V-N085S-E087D-S099R-T114Q-S126A-D127E-F128G-N242D | 39 | 1.9 | 2.5 | 3.0 |

Protease Data Table 2

| Variants | Substitutions with respect to SEQ ID No: 1 | Stability TRIS-EDTA | PAS-38 stain Cleaning | | |
|---|---|---|---|---|---|
| | | | ADW formula A | ADW formula B | ADW formula C |
| WALBSP-07011 | A037T-S039E-I043V-A047V-P054T-I080V-N085S-E087D-S099R-S126A-D127E-F128G-N242D | 39 | 2.0 | 2.2 | 2.8 |
| WALBSP-07055 | A037T-S039E-I043V-A047V-T056Y-I080V-N085S-E087D-S099R-S126A-D127E-N242D | 39 | 2.0 | 2.1 | 2.6 |
| WALBSP-07054 | A037T-S039E-I043V-T056Y-I080V-N085S-E087D-S099R-S126A-D127E-F128G-N242D | 39 | 2.0 | 2.1 | 2.7 |
| WALBSP-07030 | A037T-S039E-I043V-A047V-T056Y-I080V-N085S-E087D-S099R-T114Q-S126A-D127E-N242D | 39 | 2.0 | 2.4 | 3.0 |
| WALBSP-07062 | S039E-N085S-S099R-S126A-D127E-F128G | 40 | 2.0 | 2.5 | 2.7 |
| WALBSP-07047 | A037T-S039E-I043V-A047V-P054T-I080V-N085S-E087D-S099R-T114Q-S126A-D127E-F128G-N242D | 40 | 1.9 | 2.5 | 2.8 |
| WALBSP-06998 | A037T-S039E-I043V-A047V-P054T-T056Y-I080V-N085S-S099R-T114Q-S126A-D127E-F128G-N242D | 40 | 1.9 | 2.4 | 2.7 |
| WALBSP-07048 | A037T-S039E-I043V-A047V-P054T-T056Y-I080V-N085S-E087D-S099R-T114Q-S126A-D127E-N242D | 40 | 2.0 | 2.3 | 3.0 |
| WALBSP-07051 | A037T-S039E-I043V-A047V-P054T-T056Y-I080V-N085S-E087D-S126A-D127E-F128G-N242D | 40 | 0.7 | 0.7 | 0.8 |
| WALBSP-07045 | A037T-S039E-I043V-A047V-T056Y-I080V-N085S-E087D-S099R-S126A-F128G-N242D | 40 | 2.1 | 2.1 | 2.6 |
| WALBSP-07049 | A037T-S039E-I043V-A047V-T056Y-I080V-E087D-S099R-T114Q-S126A-D127E-F128G-N242D | 41 | 2.0 | 2.6 | 2.9 |

| | | | PAS-38 stain Cleaning | | |
|---|---|---|---|---|---|
| | Substitutions with | Stability | | | |
| Variants | respect to SEQ ID No: 1 | TRIS-EDTA | ADW formula A | ADW formula B | ADW formula C |
| WALBSP-07003 | S039E-S099R-T114Q-S126A-D127E-F128G | 41 | 2.1 | 2.3 | 2.8 |
| WALBSP-07004 | A037T-S039E-I043V-A047V-P054T-T056Y-I080V-N085S-E087D-S099R-S126A-D127E-N242D | 41 | 1.9 | 2.2 | 2.6 |
| WALBSP-07000 | A037T-S039E-I043V-A047V-T056Y-I080V-N085S-E087D-S099R-S126A-D127E-F128G-N242D | 41 | 1.9 | 2.2 | 2.7 |
| WALBSP-07028 | A037T-S039E-I043V-A047V-P054T-T056Y-I080V-N085S-E087D-S099R-T114Q-D127E-F128G-N242D | 41 | 2.1 | 2.2 | 2.7 |
| WALBSP-07059 | A037T-S039E-I043V-A047V-T056Y-I080V-N085S-S099R-T114Q-S126A-D127E-F128G-N242D | 41 | 2.0 | 2.3 | 3.0 |
| WALBSP-07022 | S039E-A047V-S099R-S126A-D127E-F128G | 41 | 2.1 | 2.5 | 2.5 |
| WALBSP-07015 | A037T-S039E-I043V-A047V-T056Y-I080V-N085S-S099R-S126A-D127E-F128G-N242D | 41 | 2.0 | 2.0 | 2.7 |
| WALBSP-07033 | A037T-S039E-I043V-A047V-T056Y-S099R-T114Q-S126A-D127E-F128G | 41 | 2.1 | 2.4 | 2.6 |
| WALBSP-07031 | A037T-S039E-I043V-A047V-P054T-T056Y-I080V-E087D-S099R-S126A-D127E-F128G-N242D | 41 | 2.0 | 2.3 | 2.8 |
| WALBSP-07032 | S039E-P054T-S099R-S126A-D127E-F128G | 41 | 3.6 | 4.1 | 4.6 |
| WALBSP-04815 | A37T-S39E-I43V-A47V-P54T-T56Y-I80V-N85S-E87D-S99R-T114Q-S126A-D127E-F128G-N242D | 36 | 2.0 | 2.3 | 2.6 |
| WALBSP-07064 | A037T-S039E-I043V-A047V-I080V-N085S-E087D-S099R-S126A-D127E-F128G-N242D | 42 | 2.0 | 1.9 | 2.4 |
| WALBSP-07005 | A037T-S039E-I043V-A047V-T056Y-I080V-E087D-S099R- | 42 | 1.9 | 2.0 | 2.5 |

| | | | PAS-38 stain Cleaning | | |
|---|---|---|---|---|---|
| Variants | Substitutions with respect to SEQ ID No: 1 | Stability TRIS-EDTA | ADW formula A | ADW formula B | ADW formula C |
| WALBSP-07010 | S126A-D127E-F128G-N242D | 42 | 2.1 | 2.6 | 2.9 |
| | A037T-S039E-I043V-A047V-T056Y-I080V-N085S-E087D-S099R-T114Q-D127E-F128G-N242D | 42 | 2.0 | 2.1 | 2.9 |
| WALBSP-07061 | A037T-S039E-I043V-A047V-P054T-T056Y-I080V-N085S-E087D-S099R-D127E-F128G-N242D | 42 | 2.0 | 2.1 | 2.9 |
| WALBSP-07072 | S039E-E087D-S099R-S126A-D127E-F128G | 42 | 2.0 | 1.9 | 2.8 |
| WALBSP-07035 | A037T-S039E-I043V-A047V-T056Y-I080V-N085S-E087D-S099R-D127E-F128G-N242D | 42 | 2.1 | 2.1 | 2.7 |
| WALBSP-07038 | A037T-S039E-I043V-A047V-P054T-T056Y-I080V-N085S-E087D-S099R-T114Q-S126A-F128G-N242D | 43 | 1.9 | 2.2 | 2.8 |
| WALBSP-07002 | A037T-S039E-S099R-S126A-D127E-F128G | 43 | 3.8 | 4.8 | 5.5 |
| WALBSP-07067 | A037T-S039E-I043V-A047V-P054T-T056Y-I080V-E087D-S099R-T114Q-S126A-D127E-F128G-N242D | 43 | 1.8 | 2.5 | 2.9 |
| WALBSP-07018 | A037T-S039E-I043V-A047V-P054T-T056Y-I080V-N085S-E087D-S099R-S126A-D127E-F128G-N242D | 43 | 1.9 | 2.2 | 2.8 |
| WALBSP-07020 | A037T-S039E-I043V-A047V-T056Y-I080V-N085S-E087D-S099R-T114Q-S126A-F128G-N242D | 43 | 2.0 | 2.7 | 3.1 |
| WALBSP-07043 | A037T-S039E-I043V-A047V-T056Y-S099R-S126A-D127E-F128G | 44 | 2.0 | 2.3 | 2.7 |
| WALBSP-07023 | A037T-S039E-I043V-A047V-P054T-T056Y-S099R-T114Q-S126A-D127E-F128G | 44 | 2.1 | 2.4 | 2.7 |
| WALBSP-07070 | A037T-S039E-A047V-P054T-T056Y-I080V-N085S-E087D- | 44 | 2.0 | 2.1 | 2.9 |

| | | | Protease Data Table 2 | | |
|---|---|---|---|---|---|
| | Substitutions with | Stability | PAS-38 stain Cleaning | | |
| Variants | respect to SEQ ID No: 1 | TRIS-EDTA | ADW formula A | ADW formula B | ADW formula C |
| | S099R-S126A-D127E-F128G-N242D | | | | |
| WALBSP-07071 | A037T-S039E-I043V-A047V-P054T-T056Y-I080V-N085S-E087D-S099R-S126A-F128G-N242D | 44 | 1.9 | 2.2 | 3.0 |
| WALBSP-07008 | A037T-S039E-I043V-A047V-P054T-T056Y-I080V-N085S-E087D-T114Q-S126A-D127E-F128G-N242D | 44 | 0.7 | 0.7 | 0.8 |
| WALBSP-07025 | A037T-S039E-I043V-A047V-T056Y-I080V-N085S-E087D-S126A-D127E-F128G-N242D | 45 | 0.8 | 0.5 | 0.7 |
| WALBSP-07009 | A037T-S039E-A047V-T056Y-I080V-N085S-E087D-S099R-T114Q-S126A-D127E-F128G-N242D | 45 | 2.1 | 2.6 | 3.2 |
| WALBSP-07075 | S039E-S099R-S126A-D127E-F128G | 45 | 1.9 | 2.3 | 2.8 |
| WALBSP-07017 | A037T-S039E-A047V-P054T-T056Y-I080V-N085S-E087D-S099R-T114Q-S126A-D127E-F128G-N242D | 45 | 2.0 | 2.4 | 2.8 |
| WALBSP-07069 | A037T-S039E-I043V-A047V-T056Y-I080V-N085S-E087D-T114Q-S126A-D127E-F128G-N242D | 46 | 0.8 | 0.3 | 1.0 |
| WALBSP-07044 | A037T-S039E-A047V-T056Y-I080V-N085S-E087D-S099R-S126A-D127E-F128G-N242D | 46 | 2.1 | 2.1 | 2.7 |
| WALBSP-07100 | S039E-S099R-S126A-D127E-F128G-Q256E | 47 | 2.3 | 3.0 | 3.8 |
| WALBSP-07013 | S039E-S099R-S126A-D127E-F128G-N242D | 47 | 2.1 | 2.2 | 2.6 |
| WALBSP-07139 | S039E-S099R-S126A-D127E-F128G-Q200L | 48 | 2.2 | 2.8 | 3.7 |
| WALBSP-07077 | A037T-S039E-I043V-A047V-P054T-T056Y-S099R-T114Q-S126A-D127E-F128G-N242D | 51 | 2.2 | 2.8 | 3.6 |
| WALBSP-07087 | A037T-S039E-I043V-A047V-P054T-T056Y-S099R-S126A- | 51 | 2.1 | 2.8 | 3.6 |

| | | Protease Data Table 2 | | | |
|---|---|---|---|---|---|
| | Substitutions with | Stability | PAS-38 stain Cleaning | | |
| Variants | respect to SEQ ID No: 1 | TRIS-EDTA | ADW formula A | ADW formula B | ADW formula C |
| | D127E-F128G-N242D | | | | |
| WALBSP-07138 | S039E-N074D-I080V-S099R-S126A-D127E-F128G | 53 | 2.3 | 2.8 | 3.8 |
| WALBSP-07021 | A037T-S039E-I043V-A047V-P054T-T056Y-N085S-E087D-S099R-S126A-D127E-F128G-N242D | 54 | 1.9 | 2.4 | 2.9 |
| WALBSP-07039 | A037T-S039E-I043V-A047V-T056Y-N085S-E087D-S099R-T114Q-S126A-D127E-F128G-N242D | 54 | 2.0 | 2.5 | 3.0 |
| WALBSP-07053 | A037T-S039E-I043V-A047V | 54 | 0.8 | 0.8 | 0.7 |
| WALBSP-07073 | A037T-S039E-I043V-A047V-N242D | 54 | 0.7 | 0.6 | 0.9 |
| WALBSP-07118 | S039E-P054T-N074D-S099R-S126A-D127E-F128G | 55 | 2.3 | 2.8 | 4.2 |
| WALBSP-07108 | S039E-A047V-N074D-S099R-S126A-D127E-F128G | 55 | 2.3 | 2.7 | 3.3 |
| WALBSP-07057 | A037T-S039E-I043V-A047V-P054T-T056Y-N085S-E087D-S099R-T114Q-S126A-D127E-F128G-N242D | 55 | 2.0 | 2.3 | 2.7 |
| WALBSP-07089 | S039E-N074D-S099R-T114Q-S126A-D127E-F128G | 55 | 2.5 | 2.8 | 3.8 |
| WALBSP-07148 | S039E-N074D-N085S-S099R-S126A-D127E-F128G | 56 | 2.3 | 3.0 | 3.4 |
| WALBSP-07074 | A037T-S039E-I043V-A047V-T056Y-N085S-E087D-S099R-S126A-D127E-F128G-N242D | 57 | 1.8 | 2.1 | 2.5 |
| WALBSP-07079 | S039E-N074D-E087D-S099R-S126A-D127E-F128G | 57 | 2.3 | 3.4 | ND |
| WALBSP-07098 | S039E-I043V-N074D-S099R-S126A-D127E-F128G | 57 | ND | 2.7 | 3.5 |
| WALBSP-07128 | S039E-T056Y-N074D-S099R-S126A-D127E-F128G | 58 | 2.2 | 3.0 | 3.6 |
| WALBSP-07099 | S039E-N074D-S099R-S126A-D127E-F128G-N242D | 77 | 2.2 | 3.0 | 3.8 |

As it can be seen from Table 2 the variants of the composition of the invention are considerable better than the parent protease for the removal of egg stains.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application and any patent application or patent to which this application claims priority or benefit thereof, is hereby incorporated herein by reference in its entirety unless expressly excluded or otherwise limited.

The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A phosphate-free automatic dishwashing cleaning composition comprising:

i) a protease variant consisting of an amino acid sequence with at least 92% identity with SEQ ID NO:1, and the amino acid sequence comprising an amino acid substitution at a position corresponding to P54T of SEQ ID NO: 1; and ii) from 10 to 50% by weight of the composition of a complexing agent system comprising less than 30% by weight of the composition of citric acid, wherein the complexing agent system comprises a complexing agent selected from the group consisting of methyl glycine diacetic acid, glutamic-N,N-diacetic acid, iminodisuccinic acid, carboxy methyl inulin and mixtures thereof.

2. The composition according to claim 1 further comprising a dispersant polymer having a calcium binding capacity of from between 30 to 250 mg of calcium per gram of dispersant polymer in accordance with the Calcium binding capacity test method.

3. The composition according to claim 2, wherein the dispersant polymer comprises both a sulfonated and carboxylated monomers.

4. The composition according to claim 3, wherein the dispersant polymer comprises from 40 wt % to 90 wt % of one or more carboxylic acid monomer and from a 5 wt % to 50 wt % sulfonic acid monomer.

5. The composition according to claim 2, further comprising a bleach present at from 10 wt % to 20 wt %.

6. The composition according to claim 5, further comprising a metal containing bleach catalyst, wherein the metal is selected from manganese, cobalt, copper, and iron.

7. The composition according to claim 1, wherein the complexing agent comprises methyl glycine diacetic acid and citric acid.

8. The composition according to claim 7, wherein a ratio of the citric acid to methyl glycine diacetic acid is from 0.5:1 to 5:1.

9. The composition according to claim 7, wherein a ratio of the citric acid to methyl glycine diacetic acid is from 0.5:1 to 2.5:1.

\* \* \* \* \*